(12) United States Patent
Sinha et al.

(10) Patent No.: US 8,609,866 B2
(45) Date of Patent: Dec. 17, 2013

(54) PRODRUGS OF INHIBITORS OF PLASMA KALLIKREIN

(75) Inventors: Sukanto Sinha, San Francisco, CA (US); Tamie Jo Chilcote, San Francisco, CA (US)

(73) Assignee: ActiveSite Pharmaceuticals, Inc., San Francisco, CA (US)

( * ) Notice: Subject to any disclaimer, the term of this patent is extended or adjusted under 35 U.S.C. 154(b) by 197 days.

(21) Appl. No.: 12/972,368

(22) Filed: Dec. 17, 2010

(65) Prior Publication Data

US 2011/0152533 A1    Jun. 23, 2011

Related U.S. Application Data

(60) Provisional application No. 61/345,045, filed on May 14, 2010, provisional application No. 61/284,478, filed on Dec. 18, 2009.

(51) Int. Cl.
C07D 231/16 (2006.01)
C07D 231/14 (2006.01)

(52) U.S. Cl.
USPC ............................................. 548/374.1

(58) Field of Classification Search
USPC ................................................. 548/374.1
See application file for complete search history.

(56) References Cited

U.S. PATENT DOCUMENTS

| | | |
|---|---|---|
| 5,998,424 A | 12/1999 | Galemmo, Jr. et al. |
| 6,337,344 B1 | 1/2002 | Defossa et al. |
| 7,144,902 B1 | 12/2006 | Baucke et al. |
| 7,625,944 B2 | 12/2009 | Sinha et al. |
| 7,977,380 B2 | 7/2011 | Sinha et al. |
| 2005/0282805 A1 | 12/2005 | Hangeland et al. |

FOREIGN PATENT DOCUMENTS

| | | |
|---|---|---|
| JP | 2001-527066 A | 12/2001 |
| JP | 2002-507968 A | 3/2002 |
| WO | 99/28297 A1 | 6/1999 |
| WO | 00/61609 A2 | 10/2000 |
| WO | 02/14270 A1 | 2/2002 |
| WO | 2006/027135 A1 | 3/2006 |
| WO | 2008/016883 A2 | 2/2008 |
| WO | 2009/097141 A1 | 8/2009 |
| WO | 2011/075684 A1 | 6/2011 |

OTHER PUBLICATIONS

Dorwald, Side Reactions in Organic Synthesis, 2005, Wiley: VCH Weinheim Preface, pp. 1-15 & Chapter 8, pp. 279-308.*
International Search Report and Written Opinion, date May 23, 2011, PCT application No. PCT/US10/61122, 11 pages.
Govers-Riemslag et al., Journal of Thromosis and Haemostasis, 2007, 5, 1896-903.
Phipps et al., Kidney International, 2008, 73, 1114-9.
Phipps et al., Hypertension, 2009, vol. 53, pp. 175-181.
Schmaier, J. Clin. Invest., 2002, 109, 1007-9.
Koshio et al, "Orally active factor Xa inhibitor: synthesis and biological activity of masked amidines as prodrugs of novel 1,4-diazepane derivatives," Bioorganic and Medicinal Chemistry, 2004, vol. 12, pp. 5415-5426.
Uchida et al., "Orally active factor Xa inhibitors. Investigation of a novel series of 3-amidinophenyl sulfonamide derivatives using an amidoxime prodrug strategy," Bioorganic and Medicinal Chemistry Letters, 2008, vol. 18, pp. 4682-4687.
Weller et al., "Orally Active Fibrinogen Receptor Antagonists. 2. Amidoximes as Prodrugs of Amidines," Journal of Medicinal Chemistry, 1996, vol. 39, pp. 3139-3147.
Extended European Search Report mailed Jun. 4, 2013 EP Application No. 10838317, 8 pages.

* cited by examiner

Primary Examiner — Patricia L Morris
(74) Attorney, Agent, or Firm — Kilpatrick Townsend & Stockton LLP; William B. Kezer

(57) ABSTRACT

The present invention provides prodrugs of compounds that inhibit the activity of plasma kallikrein (PK) and methods of preventing and treating plasma kallikrein dependent diseases or conditions, for example, diabetic macular edema, with the prodrugs having the formula:

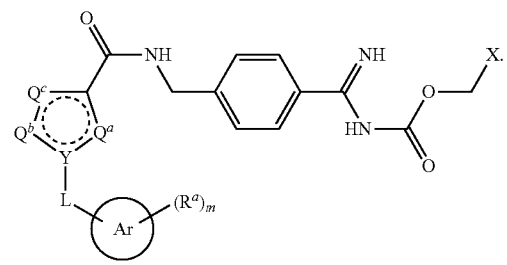

9 Claims, 6 Drawing Sheets

(Z)-methyl amino-(4-((1-(4-fluorophenyl)-2,5-dimethyl-pyrrole-3-carbonylamino)methyl)phenyl)-methylenecarbamate (Z)-methyl amino-(4-((1-benzyl-5-methyl-pyrazole-4-carbonylamino)methyl)phenyl)-methylenecarbamate

PRODRUGS OF INHIBITORS OF PLASMA KALLIKREIN

CROSS-REFERENCES TO RELATED APPLICATIONS

This application claims the benefit of U.S. Provisional Application Ser. No. 61/284,478, filed Dec. 18, 2009, and U.S. Provisional Application Ser. No. 61/345,045, filed May 14, 2010, the contents of which are incorporated herein by reference.

STATEMENT AS TO RIGHTS TO INVENTIONS MADE UNDER FEDERALLY SPONSORED RESEARCH AND DEVELOPMENT

This invention was made with United States Government support under grant R44EY019629 awarded by the National Institutes of Health to ActiveSite Pharmaceuticals, Inc. The Government has certain rights to this invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

This invention provides new pharmaceutically useful compounds that are prodrugs of compounds known to be inhibitors of the serine protease plasma kallikrein (PK). Upon administration to a subject having a disease or condition that can be treated with a plasma kallikrein inhibitor, they are converted in vivo into the active compounds, and therefore have valuable properties as pharmaceutical agents. This invention also provides new compounds that are especially useful as inhibitors of plasma kallikrein, in that they exhibit both high potency inhibiting this enzyme, and also exhibit pharmacologically desirable properties when administered in vivo.

BRIEF SUMMARY OF THE INVENTION

In one aspect, the present invention provides compounds having the formula:

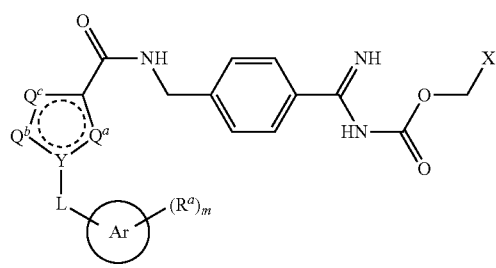

(I)

wherein Ar is a bond or an aromatic ring selected from the group consisting of benzene, pyridine and pyrimidine; the subscript m is an integer of from 0 to 5; each $R^a$ is independently selected from the group consisting of cycloalkyl, haloalkyl, halogen, —OH, —OR$^1$, —OSi(R$^1$)$_3$, —OC(O)O—R$^1$, —OC(O)R$^1$, —OC(O)NHR$^1$, —OC(O)N(R$^1$)$_2$, —SH, —SR$^1$, —S(O)R$^1$, —S(O)$_2$R$^1$, —SO$_2$NH$_2$, —S(O)$_2$NHR$^1$, —S(O)$_2$N(R$^1$)$_2$, —NHS(O)$_2$R$^1$, —NR$^1$S(O)$_2$R$^1$, —C(O)NH$_2$, —C(O)NHR$^1$, —C(O)N(R$^1$)$_2$, —C(O)R$^1$, —C(O)H, —C(=S)R$^1$, —NHC(O)R$^1$, —NR$^1$C(O)R$^1$, —NHC(O)NH$_2$, —NR$^1$C(O)NH$_2$, —NR$^1$C(O)NHR$^1$, —NHC(O)NHR$^1$, —NR$^1$C(O)N(R$^1$)$_2$, —NHC(O)N(R$^1$)$_2$, —CO$_2$H, —CO$_2$R$^1$, —NHCO$_2$R$^1$, —NR$^1$CO$_2$R$^1$, —R$^1$, —CN, —NO$_2$, —NH$_2$, —NHR$^1$, —N(R$^1$)$_2$, —NR$^1$S(O)NH$_2$, —NR$^1$S(O)$_2$NHR$^1$, —NH$_2$C(=NR$^1$)NH$_2$, —N=C(NH$_2$)NH$_2$, —C(=NR$^1$)NH$_2$, —NH—OH, —NR$^1$—OH, —N=C=O, —N=C=S, —Si(R$^1$)$_3$, —NH—NHR$^1$, —NHC(O)NHNH$_2$, NO, —N=C=NR$^1$ and —S—CN, wherein each R$^1$ is independently alkyl or aryl;

L is a linking group selected from the group consisting of a bond, CH$_2$ and SO$_2$;

$Q^a$, $Q^b$ and $Q^c$ are each members independently selected from the group consisting of N, S, O and C(R$^q$) wherein each $R^q$ is independently selected from the group consisting of H, $C_{1-8}$ alkyl and phenyl;

Y is a member selected from the group consisting of C and N; and the ring having $Q^a$, $Q^b$, $Q^c$ and Y as ring vertices is a five-membered ring having two double bonds;

and when Ar is a bond, m is 1; when Ar is an aromatic ring, m is an integer of from 0-5;

X is a member selected from the group consisting of H, $C_{1-8}$ alkyl and phenyl; and pharmaceutically acceptable salts thereof.

The compounds of general formula I are prodrugs of the plasma kallikrein inhibitor compounds of general formula II (see, WO 2008/016883, and U.S. Pat. No. 7,625,944). Upon administration to a subject in need of treatment with a plasma kallikrein inhibitor, the compounds of the present invention are converted in vivo into compounds of general formula II, and therefore have valuable properties as pharmaceutical agents.

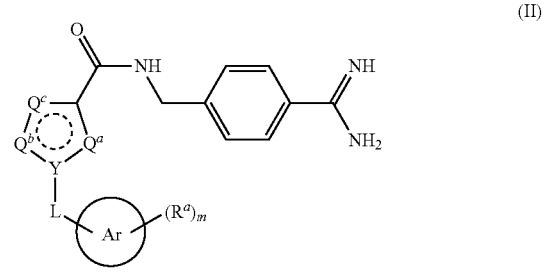

(II)

The symbols $Q_a$, $Q_b$, $Q_c$, Y, L, Ar, $R^a$ and m in general formula II have the same meaning as in general formula I.

The following are mentioned as examples of particularly preferred compounds of general formula I:

(a) (Z)-hexyl amino-(4-((1-benzylpyrazole-4-carbonylamino)methyl)phenyl)methylenecarbamate (b) (Z)-hexyl amino-(4-((2,5-dimethyl-1-(4-pyridylmethyl)pyrrole-3-carbonylamino)methyl)phenyl)methylenecarbamate (c) (Z)-hexyl amino-(4-((1-4-fluorophenyl-2,5-dimethylpyrrole-3-carbonylamino)methyl)phenyl)methylenecarbamate (d) (Z)-hexyl amino-(4-((1-4-chlorophenyl-2,5-dimethylpyrrole-3-carbonylamino)methyl)phenyl)methylenecarbamate (e) (Z)-hexyl amino-(4-((1-4-methoxyphenyl-2,5-dimethyl-pyrrole-3-carbonylamino)methyl)phenyl)methylenecarbamate (f) (Z)-methyl amino-(4-((1-4-methoxyphenyl-2,5-dimethyl-pyrrole-3-carbonylamino)methyl)phenyl)methylenecarbamate (g) (Z)-methyl amino(4-((1-4-chlorophenyl-2,5-dimethyl-pyrrole-3-carbonylamino)methyl)phenyl)methylenecarbamate (h) (Z)-methyl amino-(4-((1-4-fluorophenyl-2,5-dimethyl-pyrrole-3-carbonylamino)methyl)phenyl)methylenecarbamate (i) (Z)-methyl amino-(4-((2,5-dimethyl-1-4-pyridylmethylpyrrole-3-carbonylamino)methyl)phenyl)methylenecarbamate (j) (Z)-methyl amino-(4-((1-benzylpyrazole-4-carbonylamino)methyl)phenyl)methylenecarbamate (k) (Z)-benzyl amino-(4-((1-benzylpyrazole-4-carbonylamino)methyl)phenyl)methylenecarbamate (l) (Z)-benzyl amino-(4-((1-benzylpyrazole-4-carbonylamino)methyl)phenyl)methylenecarbamate (m) (Z)-benzyl amino-(4-((1-(4-fluorophenyl)-2,5-dimethyl-pyrrole-3-carbonylamino)methyl)phenyl)methylenecarbamate (n) (Z)-benzyl amino-(4-((1-(4-chlorophenyl)-2,5-dimethyl-pyrrole-3-carbonylamino)methyl)phenyl)methylenecarbamate (o) (Z)-benzyl amino-(4-((1-(4-methoxyphenyl)-2,5-dimethyl-pyrrole-3-carbonylamino)methyl)phenyl)methylenecarbamate (p) (Z)-ethyl amino-(4-((1-(4-methoxyphenyl)-2,5-dimethyl-pyrrole-3-carbonylamino)methyl)phenyl)methylenecarbamate (q) (Z)-ethyl amino-(4-((1-(4-chlorophenyl)-2,5-dimethyl-pyrrole-3-carbonylamino)methyl)phenyl)methylenecarbamate (r) (Z)-ethyl amino-(4-((1-(4-fluorophenyl)-2,5-dimethyl-pyrrole-3-carbonylamino)methyl)phenyl)methylenecarbamate (s) (Z)-ethyl amino-(4-((2,5-dimethyl-1-(4-pyridylmethyl)pyrrole-3-carbonylamino)methyl)phenyl)methylenecarbamate (t) (Z)-ethyl amino-(4-((1-benzylpyrazole-4-carbonylamino)methyl)phenyl)methylenecarbamate (u) (Z)-propyl amino-(4-((1-(4-methoxyphenyl)-2,5-dimethyl-pyrrole-3-carbonylamino)methyl)phenyl)methylenecarbamate (v) (Z)-propyl amino-(4-((1-(4-chlorophenyl)-2,5-dimethyl-pyrrole-3-carbonylamino)methyl)phenyl)methylenecarbamate (w) (Z)-propyl amino-(4-((1-(4-fluorophenyl)-2,5-dimethyl-pyrrole-3-carbonylamino)methyl)phenyl)methylenecarbamate (x) (Z)-propyl amino-(4-((2,5-dimethyl-1-(4-pyridylmethyl)pyrrole-3-carbonylamino)methyl)phenyl)methylenecarbamate (y) (Z)-propyl amino-(4-((1-benzylpyrazole-4-carbonylamino)methyl)phenyl)methylenecarbamate In another aspect, the present invention provides a compound having the formula:

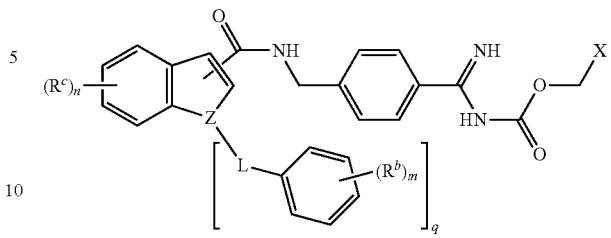

(III)

wherein the subscript m is an integer of from 0 to 5; the subscript n is an integer of from 0 to 4; the subscript q is an integer of from 0 to 1; L is a linking group selected from the group consisting of a bond, $CH_2$ and $SO_2$; each of $R^b$ and $R^c$ is independently selected from the group consisting of cycloalkyl, haloalkyl, halogen, —OH, —$OR^2$, —$OSi(R^2)_3$, —OC(O)O—$R^2$, —OC(O)$R^2$, —OC(O)NH$R^2$, —OC(O)N($R^2$)$_2$, —SH, —S$R^2$, —S(O)$R^2$, —S(O)$_2R^2$, —SO$_2$NH$_2$, —S(O)$_2$NH$R^2$, —S(O)$_2$N($R^2$)$_2$, —NHS(O)$_2R^2$, —N$R^2$S(O)$_2R^2$, —C(O)NH$_2$, —C(O)NH$R^2$, —C(O)N($R^2$)$_2$, —C(O)$R^2$, —C(O)H, —C(=S)$R^2$, —NHC(O)$R^2$, —N$R^2$C(O)$R^2$, —NHC(O)NH$_2$, —N$R^2$C(O)NH$_2$, —N$R^2$C(O)NH$R^2$, —NHC(O)NH$R^2$, —N$R^2$C(O)N($R^2$)$_2$, —NHC(O)N($R^2$)$_2$, —CO$_2$H, —CO$_2R^2$, —NHCO$_2R^2$, —N$R^2$CO$_2R^2$, —$R^2$, —CN, —NO$_2$, —NH$_2$, —NH$R^2$, —N($R^2$)$_2$, —N$R^2$S(O)NH$_2$, —N$R^2$S(O)$_2$NH$R^2$, —NH$_2$C(=N$R^2$)NH$_2$, —N=C(NH$_2$)NH$_2$, —C(=N$R^2$)NH$_2$, —NH—OH, —N$R^2$—OH, —N$R^2$—O$R^2$, —N=C=O, —N=C=S, —Si($R^2$)$_3$, —NH—NH$R^2$, —NHC(O)NHNH$_2$, NO, —N=C=N$R^2$ and —S—CN, wherein each $R^2$ is independently alkyl or aryl; when q is 0, Z is a member selected from the group consisting of O, S and N$R^d$ wherein $R^d$ is H or $C_1$-$C_8$ alkyl; when q is 1, Z is N;

X is a member selected from the group consisting of H, $C_{1-8}$ alkyl, and phenyl;

and pharmaceutically acceptable salts thereof.

The compounds of general formula III are prodrugs of the plasma kallikrein inhibitor compounds of general formula IV (see, WO 2008/016883, and U.S. Pat. No. 7,625,944). Upon administration to a subject in need of treatment with a plasma kallikrein inhibitor, they are converted in vivo into compounds of general formula IV, and therefore have valuable properties as pharmaceutical agents.

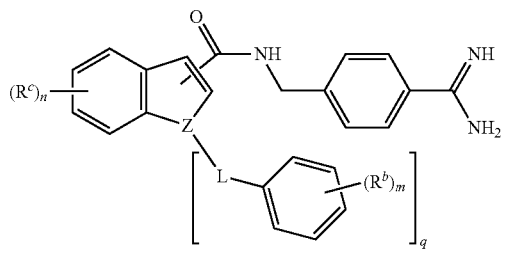

(IV)

The symbols $R^b$, $R^c$, L, Z, m, n and q in general formula IV have the same meaning as in general formula III.

The following are mentioned as examples of particularly preferred compounds of general formula III:

(a) (Z)-methyl amino(4-((1-benzylindole-3-carbonylamino)methyl)phenyl)methylenecarbamate (b) (Z)-methyl amino(4-((1-(benzenesulfonyl)indole-3-carbonylamino)methyl)phenyl)methylenecarbamate
(c) (Z)-ethyl amino(4-((1-benzylindole-3-carbonylamino)methyl)phenyl)methylenecarbamate
(d) (Z)-ethyl amino(4-((1-(benzenesulfonyl)indole-3-carbonylamino)methyl)phenyl)methylenecarbamate In another aspect, the present invention provides compounds of the general formula V:

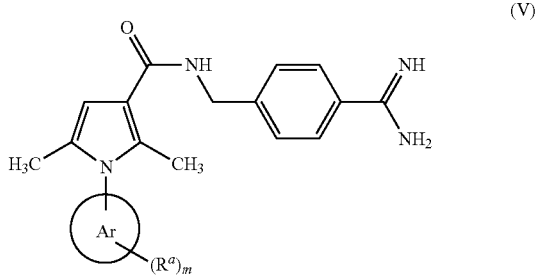

(V)

where Ar is a ring selected from benzene, pyridine, pyrimidine or a five-membered heteroaryl ring, $R^a$ has the same meaning as in general formula I, and m is an integer of 1-5 when Ar is benzene, 0-4 when Ar is pyridine, 0-3 when Ar is pyrimidine, and 0-2 when Ar is a five-membered heteroaryl ring.

The following are mentioned as examples of particularly preferred compounds of general formula V:
(a) N-[(4-carbamimidoylphenyl)methyl]-1-(4-fluorophenyl)-2,5-dimethyl-pyrrole-3-carboxamide
(b) N-[(4-carbamimidoylphenyl)methyl]-1-(2-fluorophenyl)-2,5-dimethyl-pyrrole-3-carboxamide
(c) N-[(4-carbamimidoylphenyl)methyl]-1-(4-methoxyphenyl)-2,5-dimethyl-pyrrole-3-carboxamide
(d) N-[(4-carbamimidoylphenyl)methyl]-1-(4-chlorophenyl)-2,5-dimethyl-pyrrole-3-carboxamide
(e) N-[(4-carbamimidoylphenyl)methyl]-1-(2,3-dihydro-1,4-benzodioxin-6-yl)-2,5-dimethyl-pyrrole-3-carboxamide
(f) N-[(4-carbamimidoylphenyl)methyl]-2,5-dimethyl-1-(3-pyridyl)pyrrole-3-carboxamide
(g) N-[(4-carbamimidoylphenyl)methyl]-2,5-dimethyl-1-(2-pyridyl)pyrrole-3-carboxamide
(h) N-[(4-carbamimidoylphenyl)methyl]-2,5-dimethyl-1-thiazol-2-yl-pyrrole-3-carboxamide.

In yet another aspect, the present invention provides a pharmaceutical composition. The composition includes a compound of formula I, III or V, in combination with a pharmaceutically acceptable excipient.

In a further aspect, the present invention provides a method of treating conditions associated with diabetes and hypertension, e.g., retinopathy, macular edema, nephropathy, neuropathy and elevated blood pressure.

In another aspect, the present invention provides a method of treating a clinical condition that is caused by or is aggravated by excessive vascular permeability and consequent edema, e.g., ischemic and hemorrhagic stroke, diabetic macular edema, cystoid macular edema, retinal vein occlusions, age-related macular degeneration, head trauma, capillary leak syndrome, and glioblastoma multiforme.

In still another aspect, the present invention provides a method of treating a plasma kallikrein-related disorder or condition in a subject in need thereof. The method includes administering to the subject a compound of formula I, III or V.

DETAILED DESCRIPTION OF THE INVENTION

I. Definitions

Figure 1A:
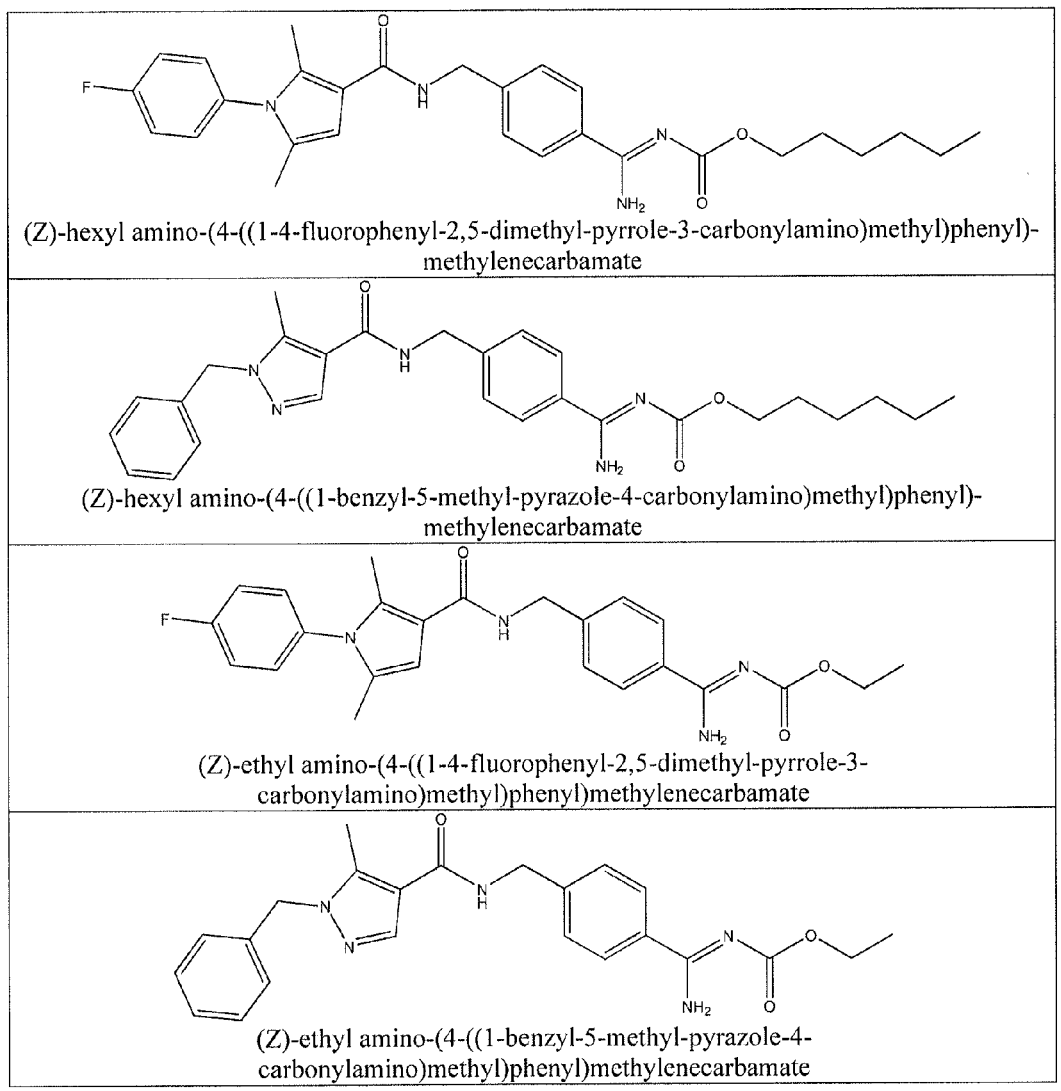
FIGS. 1A and 1B provide structures for selected compounds of the invention.
Figure 1B:
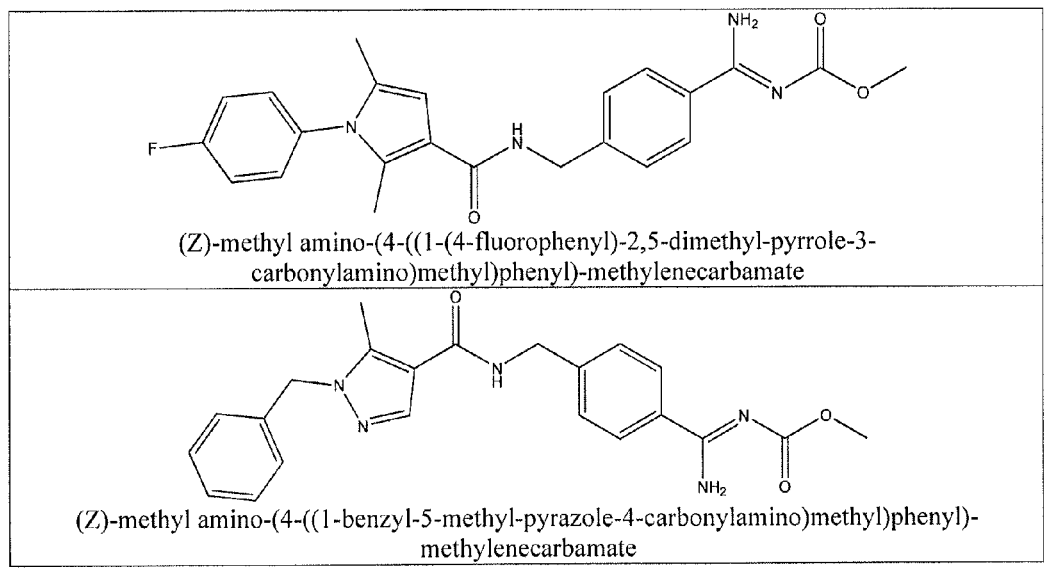
Figure 2A:
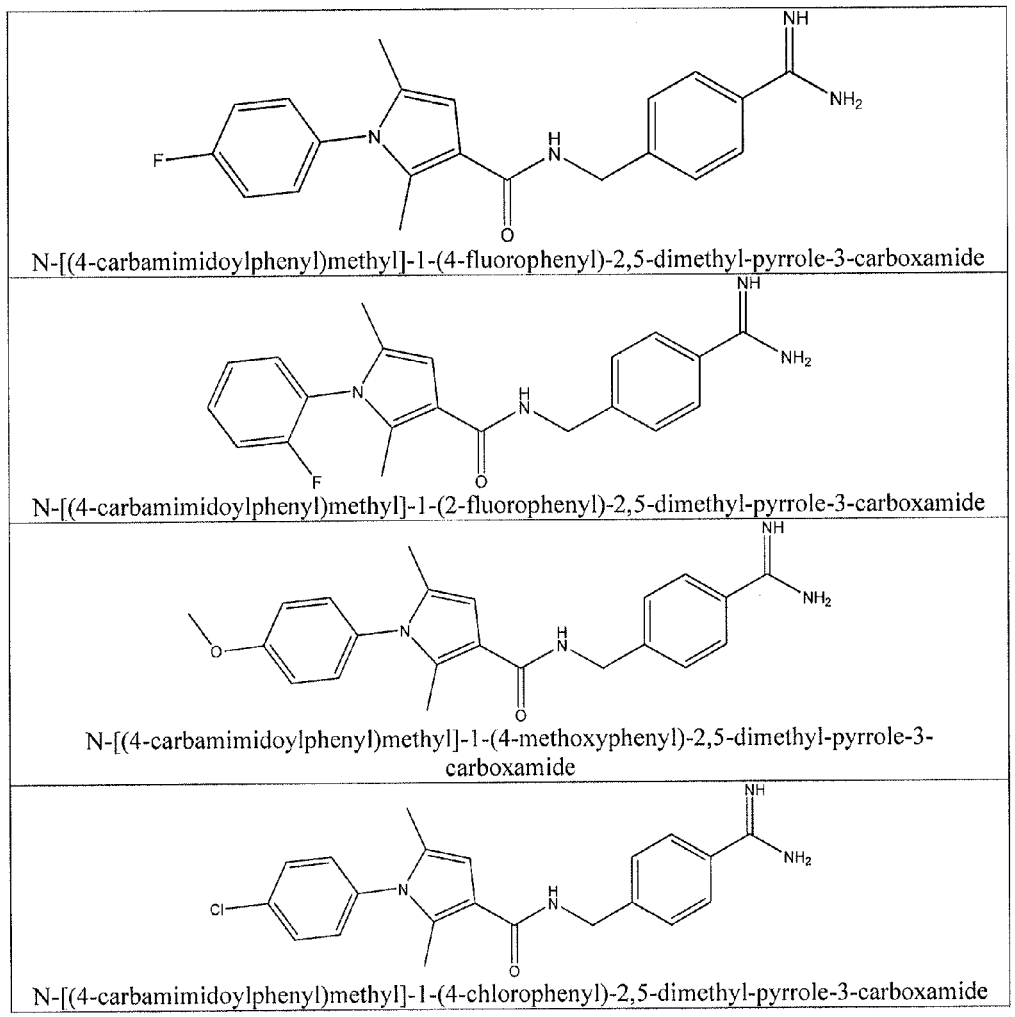
FIGS. 2A and 2B provide structures for selected compounds of the invention.
Figure 2B:
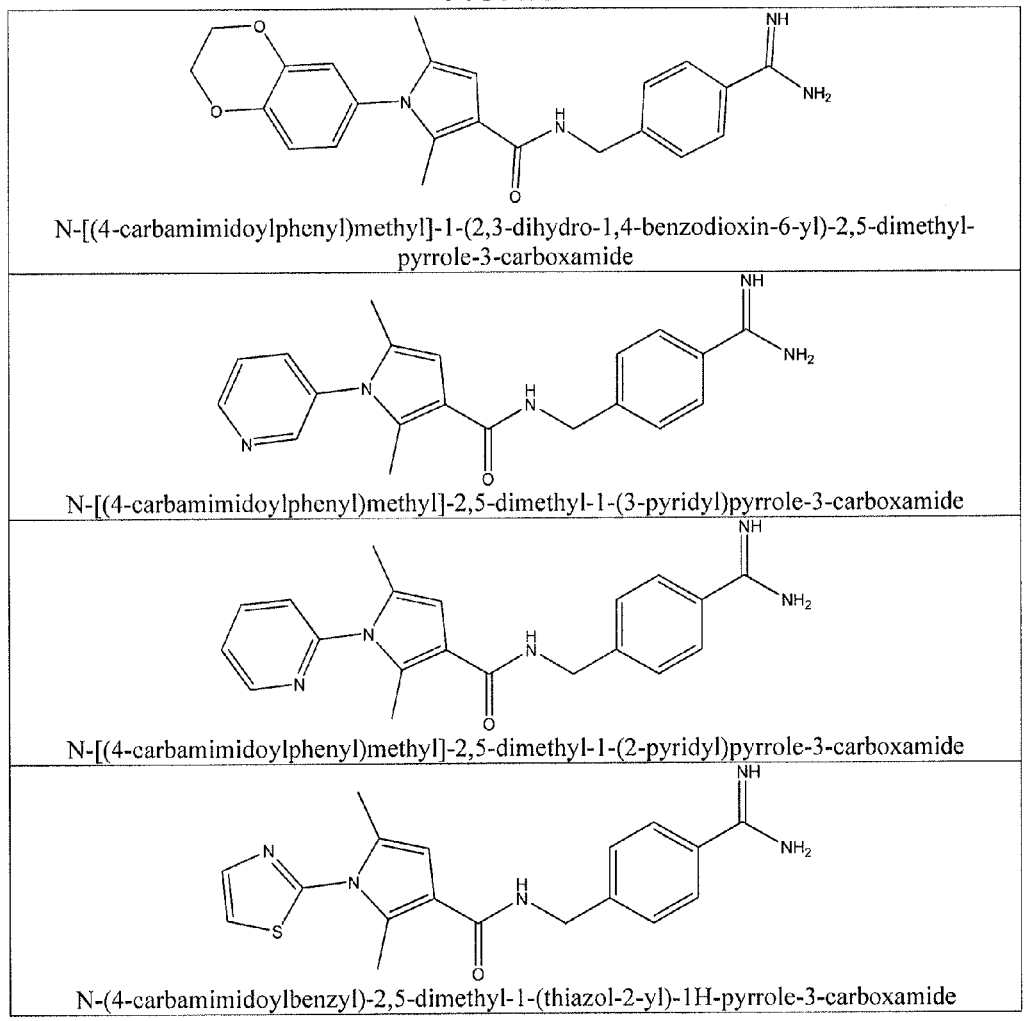
Figure 3A:
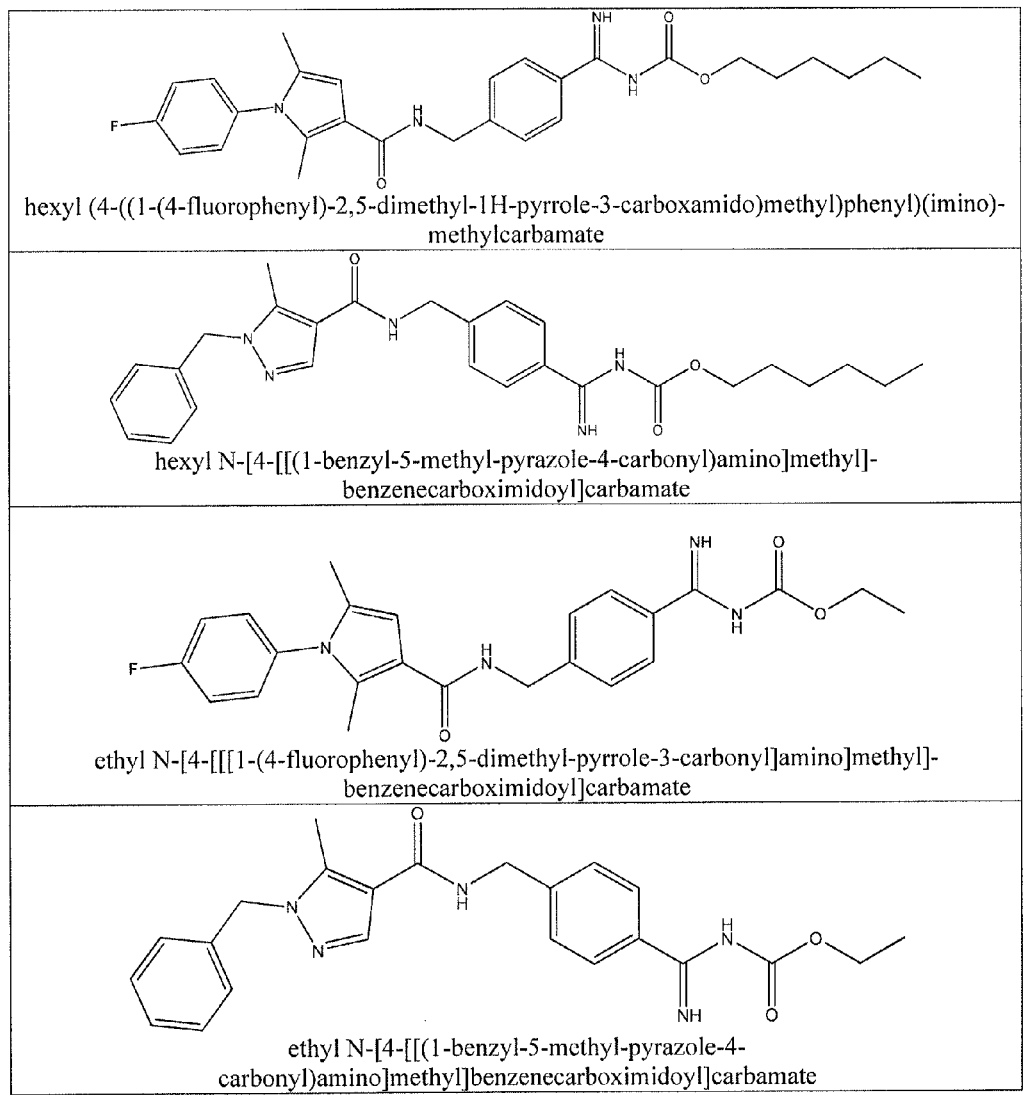
FIGS. 3A and 3B provide tautomer structures for selected compounds provided in FIGS. 1A and 1B.
Figure 3B:
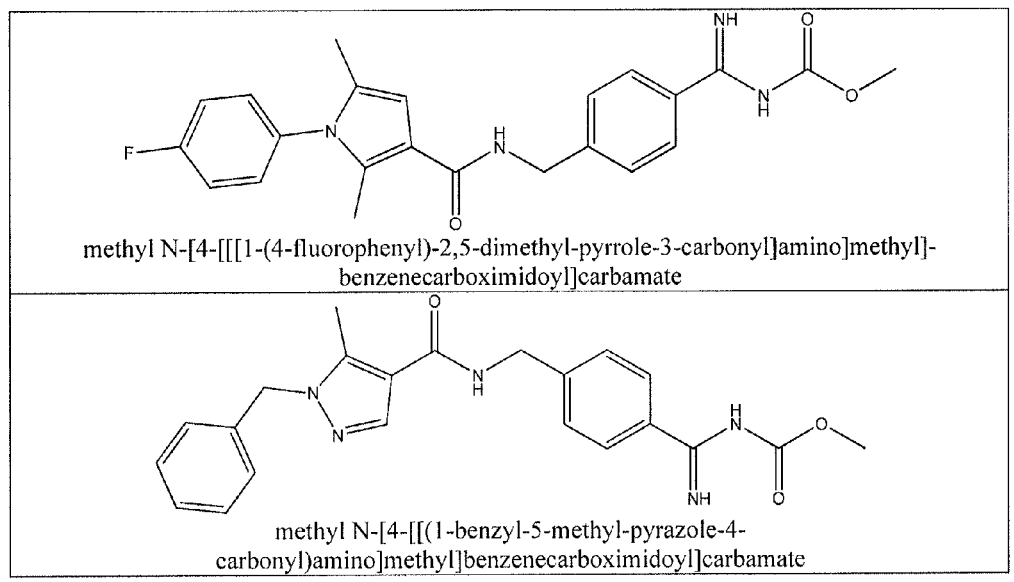

Unless otherwise stated the following terms used in the specification and claims have the meanings given below.

Compound names were generated using the software program, ChemBioDraw, Level Ultra, version 11.0.1.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl), when a prefix is not included to indicate the number of main chain carbon atoms in an alkyl portion, the radical or portion thereof will have 12 or fewer main chain carbon atoms.

The term "alkylene" by itself or as part of another substituent means a divalent radical derived from an alkane, as exemplified by —CH₂CH₂CH₂CH₂—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The term "cycloalkyl" refers to hydrocarbon rings having the indicated number of ring atoms (e.g., $C_{3-6}$cycloalkyl) and being fully saturated or having no more than one double bond between ring vertices. One or two C atoms may optionally be replaced by a carbonyl. "Cycloalkyl" is also meant to refer to bicyclic and polycyclic hydrocarbon rings such as, for example, bicyclo[2.2.1]heptane, bicyclo[2.2.2]octane, etc. When a prefix is not included to indicate the number of ring carbon atoms in a cycloalkyl, the radical or portion thereof will have 8 or fewer ring carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$haloalkyl" is mean to include trifluoromethyl, 2,2,2-trifluoroethyl, 4-chlorobutyl, 3-bromopropyl, and the like.

The term "aryl" means a monovalent monocyclic, bicyclic or polycyclic aromatic hydrocarbon radical of 5 to 14 ring atoms which is unsubstituted or substituted independently with one to four substituents, preferably one, two, or three substituents selected from alkyl, cycloalkyl, cycloalkyl-alkyl, halo, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkylalkyl, phenyl or phenylalkyl, aryl or arylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl, aryl or arylalkyl) or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl, aryl or arylalkyl). More specifically the term aryl includes, but is not limited to, phenyl, biphenyl, 1-naphthyl, and 2-naphthyl, and the substituted forms thereof. Similarly, the term "heteroaryl" refers to those aryl groups wherein one to five heteroatoms or heteroatom functional groups have replaced a ring carbon, while retaining aromatic properties, e.g., pyridyl, quinolinyl, quinazolinyl, thienyl, and the like. The heteroatoms are selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. For brevity, the term aryl, when used in combination with other radicals (e.g., aryloxy, arylalkyl) is meant to include both aryl groups and heteroaryl groups as described above.

Substituents for the aryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)═NH, —NR'C(NH$_2$)═NH, —NH—C(NH$_2$)═NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—W—(CH$_2$)$_t$—, where s and t are independently integers of from 0 to 3, and W is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The term "pharmaceutically acceptable" is meant the carrier, diluent or excipient must be compatible with the other ingredients of the formulation and not deleterious to the recipient thereof.

The term "composition" as used herein is intended to encompass a product comprising the specified ingredients in the specified amounts, as well as any product which results, directly or indirectly, from combination of the specified ingredients in the specified amounts.

The term "subject" as used herein is meant to include animals, such as mammals, including, but are not limited to, primates (e.g. humans), cows, sheep, goats, horses, dogs, cats, rabbits, rats, mice and the like.

II. General

The present invention relates to and methods of using the compounds and pharmaceutical compositions for the prevention and treatment of plasma kallikrein-dependent diseases or conditions. Therefore, diseases or conditions that can be treated using the compounds of the present invention include, but are not limited to, ischemic stroke, hemorrhagic stroke, hypertension and its vascular complications (especially retinopathy and nephropathy), cerebrovascular edema, pulmonary hypertension, inflammation, pain, acute myocardial infarction (MI), deep vein thrombosis (DVT), complications from fibrinolytic treatment (e.g., with tissue plasminogen activator, streptokinase) following stroke or MI, angina, angioedema, sepsis, arthritis, complications of cardiopulmonary bypass, capillary leak syndrome, inflammatory bowel disease, diabetes and its vascular complications (especially retinopathy, diabetic macular edema, nephropathy and neuropathy), age-related macular degeneration, retinal vein occlusions, brain edema, ischemia-reperfusion injury, angiogenesis (e.g., in cancer), asthma, anaphylaxis, and cerebrovascular complications of neurological conditions (e.g., Alzheimer's Disease, Parkinson's Disease, multiple sclerosis, CNS infections, and glioblastoma multiforme).

III. Compounds

In one aspect, the present invention provides compounds having the formula:

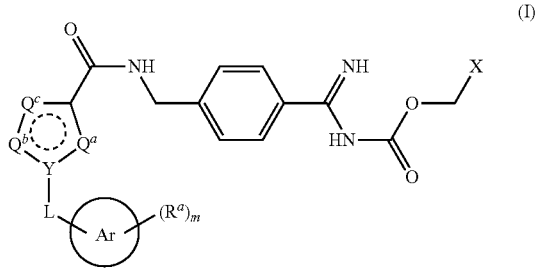

(I)

wherein Ar is a bond or an aromatic ring selected from the group consisting of benzene, pyridine and pyrimidine. When Ar is a bond, m is 1. When Ar is an aromatic ring, m is an integer from 0-5. In one embodiment, Ar is benzene or pyridine. In another embodiment, Ar is a bond.

X is a member selected from the group consisting of H, $C_{1-8}$ alkyl and phenyl. In one embodiment, X is H. In another embodiment, X is $C_5$ alkyl. In still another embodiment, X is phenyl.

The subscript m is an integer from 0 to 5. In one embodiment, m is 0.

Each $R^a$ is independently selected from the group consisting of cycloalkyl, haloalkyl, halogen, —OH, —$OR^1$, —OSi$(R^1)_3$, —OC(O)O—$R^1$, —OC(O)$R^1$, —OC(O)NH$R^1$, —OC(O)N($R^1)_2$, —SH, —$SR^1$, —S(O)$R^1$, —S(O)$_2R^1$, —SO$_2$NH$_2$, —S(O)$_2$NH$R^1$, —S(O)$_2$N($R^1)_2$, —NHS(O)$_2R^1$, —$NR^1$S(O)$_2R^1$, —C(O)NH$_2$, —C(O)NH$R^1$, —C(O)N($R^1)_2$, —C(O)R', —C(O)H, —C(=S)$R^1$, —NHC(O)$R^1$, —$NR^1$C(O)$R^1$, —NHC(O)NH$_2$, —$NR^1$C(O)NH$_2$, —$NR^1$C(O)NH$R^1$, —NHC(O)NH$R^1$, —$NR^1$C(O)N($R^1)_2$, —NHC(O)N($R^1)_2$, —CO$_2$H, —CO$_2R^1$, —NHCO$_2R^1$, —$NR^1$CO$_2R^1$, —$R^1$, —CN, —NO$_2$, —NH$_2$, —NH$R^1$, —N($R^1)_2$, —$NR^1$S(O)NH$_2$, —$NR^1$S(O)$_2$NH$R^1$, —NH$_2$C(=$NR^1$)NH$_2$, —N=C(NH$_2$)NH$_2$, —C(=$NR^1$)NH$_2$, —NH—OH, —$NR^1$—OH, —$NR^1$—$OR^1$, —N=C=O, —N=C=S, —Si($R^1)_3$, —NH—NH$R^1$, —NHC(O)NHNH$_2$, NO, —N=C=$NR^1$ and —S—CN, wherein each $R^1$ is independently alkyl or aryl. In one embodiment, $R^1$ is $C_1$-$C_8$ alkyl. In another embodiment, $R^1$ is unsubstituted aryl, such as phenyl or pyridyl, or a substituted aryl, such as a substituted phenyl or a substituted pyridyl.

In one embodiment, each $R^a$ is independently selected from the group consisting of $C_1$-$C_8$ alkyl, $C_1$-$C_8$ alkoxy, aryl, aryl($C_1$-$C_8$ alkyl), halogen, —NH$_2$, —NH($C_1$-$C_8$ alkyl), —N($C_1$-$C_8$ alkyl)$_2$, —CN, —C(=O)($C_1$-$C_8$ alkyl), —(C=O)NH$_2$, —(C=O)NH($C_1$-$C_8$ alkyl), —C(=O)N($C_1$-$C_8$ alkyl)$_2$, —OH, —COOH, —COO($C_1$-$C_8$ alkyl), —OCO($C_1$-$C_8$ alkyl), —O(C=O)O($C_1$-$C_8$alkyl)-NO$_2$, —SH, —S($C_1$-$C_8$ alkyl), —NH(C=O)($C_1$-$C_8$alkyl), —NH(C=O)O($C_1$-$C_8$alkyl), —O(C=O)NH($C_1$-$C_8$ alkyl), —SO$_2$($C_1$-$C_8$ alkyl), —NHSO$_2$($C_1$-$C_8$ alkyl) and —SO$_2$NH($C_1$-$C_8$ alkyl). In another embodiment, each $R^a$ is independently selected from the group consisting of $C_1$-$C_8$ alkyl, $C_1$-$C_8$ alkoxy, phenyl, phenyl($C_1$-$C_8$ alkyl), halogen, —CN, —NH$_2$, —NH($C_1$-$C_8$ alkyl), —N($C_1$-$C_8$ alkyl)$_2$, —(C=O)CH$_3$, —(C=O)NH$_2$, —OH, —COOH, —COO($C_1$-$C_8$ alkyl), —OCO($C_1$-$C_8$ alkyl), —O(C=O)O($C_1$-$C_8$alkyl), —NO$_2$, —SH, —S($C_1$-$C_8$ alkyl), and —NH(C=O)($C_1$-$C_8$alkyl). In yet another embodiment, each $R^a$ is independently selected from the group consisting of $C_1$-$C_8$ alkyl, $C_1$-$C_8$ alkoxy, phenyl, phenyl($C_1$-$C_8$ alkyl), phenoxy, aryloxy, halogen, —CN, —NH$_2$, —NH-aryl, —(C=O)CH$_3$, —(C=O)NH$_2$, —OH, —COOH, —COO($C_1$-$C_8$ alkyl), —OCO($C_1$-$C_8$ alkyl), —COO-aryl, —OC(O)-aryl, —O(C=O)O($C_1$-$C_8$alkyl)-NO$_2$, —SH, —S($C_1$-$C_8$ alkyl), —NH(C=O)($C_1$-$C_8$ alkyl) and the like. For example, $R^a$ is halogen, such as Cl, Br or I.

L is a linking group selected from the group consisting of a bond, CH$_2$ and SO$_2$.

$Q^a$, $Q^b$, and $Q^c$ are each members independently selected from the group consisting of N, S, O and C($R^q$) wherein each $R^q$ is independently selected from the group consisting of H, $C_{1-8}$ alkyl, halogen and phenyl.

Y is selected from C and N; and the ring having $Q^a$, $Q^b$, $Q^c$ and Y as ring vertices is a five-membered ring having two double bonds.

In a first group of embodiments, $Q^a$ is N and $Q^b$ and $Q^c$ are each selected from N, O and C($R^q$). In certain instances, $Q^a$ is N and $Q^c$ and $Q^b$ are each independently selected from N and C($R^q$). In certain other instances, $Q^a$ is N and $Q^c$ and $Q^b$ are each selected from C($R^q$) and O. In yet certain other instances, $Q^a$ is N, $Q^c$ is a member selected from N and O, and $Q^b$ is the other member selected from N and O.

In a second group of embodiments, $Q^a$ is O and $Q^b$ and $Q^c$ are each selected from N, O and C($R^q$). In certain instances, $Q^a$ is O and $Q^c$ and $Q^b$ are each independently selected from N and C($R^q$).

In a third group of embodiments, $Q^a$ is C($R^q$) and $Q^b$ and $Q^c$ are each selected from N, O and C($R^q$). In certain instances, $Q^a$ is C($R^q$) and $Q^b$ and $Q^c$ are each independently selected from N and O. In certain other instances, $Q^a$ is C($R^q$) and $Q^b$ and $Q^c$ are each independently selected from N and C($R^q$). In yet certain other instances, $Q^a$ is C($R^q$) and $Q^b$ and $Q^c$ are each independently selected from O and C($R^q$). In one occurrence, $Q^a$ is C($R^q$), $Q^b$ is O and $Q^c$ is (C$R^q$).

In one embodiment, Y is C, $Q^a$ is S and Ar is selected from phenyl or pyridyl. In another embodiment, Y is N, $Q^a$, $Q^b$ and $Q^c$ are each independently C($R^q$), wherein $R^q$ is H or $C_{1-8}$alkyl. In one instance, Y is N, $Q^a$ and $Q^c$ are C($R^q$) and $Q^b$ is CH. In a preferred embodiment, Y is N.

In one embodiment, L is a bond, Y is N. In another embodiment, L is a bond, Y is N and Ar is a benzene ring. In yet another embodiment, L is CH$_2$ and Y is N. In still another embodiment, L is a bond and Y is C. In a further embodiment, L is SO$_2$ and Y is N.

In a preferred embodiment, $Q^a$, $Q^b$ and $Q^c$ are each independently $CR^q$. In another preferred embodiment, L is a bond or $CH_2$. In still another preferred embodiment, Ar is benzene. In still another preferred embodiment, $R^a$ is —H and $C_1$-$C_8$ alkyl.

In each of the above embodiments, X is a member selected from the group consisting of H, $C_{1-8}$ alkyl and phenyl.

In another embodiment, the compounds of formula I have a subformula Ia:

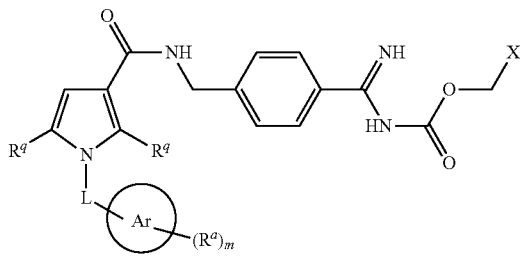

(Ia)

wherein $R^q$, L and X are as defined above. In one instance, $R^q$ is independently —H or $C_{1-8}$ alkyl and L is a bond or —$CH_2$—. In another instance, $R^a$ is $C_1$-$C_8$ haloalkyl. For example, $R^a$ is —$CF_3$ or —$CH_2CF_3$.

In one embodiment, the compounds of formula I have a subformula Ib:

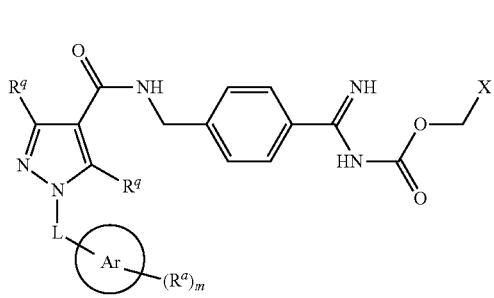

(Ib)

wherein Ar is an aromatic ring. In one instance, each $R^q$ is independently H, $C_1$-$C_8$ alkyl or halogen. In another instance, L is a bond or $CH_2$. In yet another instance, Ar is benzene. In still another instance, m is 0. In one occurrence, each $R^q$ is H, L is $CH_2$, Ar is benzene and m is 0. In another occurrence, each $R^q$ is H, L is a bond, Ar is benzene and m is 0. In each instance or occurrence, X is independently selected from the group consisting of H, $C_{1-8}$ alkyl, and phenyl.

The following are mentioned as examples of particularly preferred compounds of general formula I:
(a) (Z)-hexyl amino-(4-((1-benzylpyrazole-4-carbonylamino)methyl)phenyl)methylenecarbamate
(b) (Z)-hexyl amino-(4-((2,5-dimethyl-1-(4-pyridylmethyl)pyrrole-3-carbonylamino)methyl)phenyl)methylenecarbamate
(c) (Z)-hexyl amino-(4-((1-(4-fluorophenyl)-2,5-dimethyl-pyrrole-3-carbonylamino)methyl)phenyl)methylenecarbamate
(d) (Z)-hexyl amino-(4-((1-(4-chlorophenyl)-2,5-dimethyl-pyrrole-3-carbonylamino)methyl)phenyl)methylenecarbamate
(e) (Z)-hexyl amino-(4-((1-(4-methoxyphenyl)-2,5-dimethyl-pyrrole-3-carbonylamino)methyl)phenyl)methylenecarbamate
(f) (Z)-methyl amino-(4-((1-(4-methoxyphenyl)-2,5-dimethyl-pyrrole-3-carbonylamino)methyl)phenyl)methylenecarbamate
(g) (Z)-methyl amino-(4-((1-(4-chlorophenyl)-2,5-dimethyl-pyrrole-3-carbonylamino)methyl)phenyl)methylenecarbamate
(h) (Z)-methyl amino-(4-((1-(4-fluorophenyl)-2,5-dimethyl-pyrrole-3-carbonylamino)methyl)phenyl)methylenecarbamate
(i) (Z)-methyl amino-(4-((2,5-dimethyl-1-(4-pyridylmethyl)pyrrole-3-carbonylamino)methyl)phenyl)methylenecarbamate
(j) (Z)-methyl amino-(4-((1-benzylpyrazole-4-carbonylamino)methyl)phenyl)methylenecarbamate
(k) (Z)-benzyl amino-(4-((1-benzylpyrazole-4-carbonylamino)methyl)phenyl)methylenecarbamate
(l) (Z)-benzyl amino-(4-((2,5-dimethyl-1-(4-pyridylmethyl)pyrrole-3-carbonylamino)methyl)phenyl)methylenecarbamate
(m) (Z)-benzyl amino-(4-((1-(4-fluorophenyl)-2,5-dimethyl-pyrrole-3-carbonylamino)methyl)phenyl)methylenecarbamate
(n) (Z)-benzyl amino-(4-((1-(4-chlorophenyl)-2,5-dimethyl-pyrrole-3-carbonylamino)methyl)phenyl)methylenecarbamate
(o) (Z)-benzyl amino-(4-(1-(4-methoxyphenyl)-2,5-dimethyl-pyrrole-3-carbonylamino)phenyl)methylenecarbamate
(p) (Z)-ethyl amino-(4-((1-(4-methoxyphenyl)-2,5-dimethyl-pyrrole-3-carbonylamino)methyl)phenyl)methylenecarbamate
(q) (Z)-ethyl amino-(4-((1-(4-chlorophenyl)-2,5-dimethyl-pyrrole-3-carbonylamino)methyl)phenyl)methylenecarbamate
(r) (Z)-ethyl amino-(4-((1-(4-fluorophenyl)-2,5-dimethyl-pyrrole-3-carbonylamino)methyl)phenyl)methylenecarbamate
(s) (Z)-ethyl amino-(4-((2,5-dimethyl-1-(4-pyridylmethyl)pyrrole-3-carbonylamino)methyl)phenyl)methylenecarbamate
(t) (Z)-ethyl amino-(4-((1-benzylpyrazole-4-carbonylamino)methyl)phenyl)methylenecarbamate
(u) (Z)-propyl amino-(4-((1-(4-methoxyphenyl)-2,5-dimethyl-pyrrole-3-carbonylamino)methyl)phenyl)methylenecarbamate
(v) (Z)-propyl amino-(4-((1-(4-chlorophenyl)-2,5-dimethyl-pyrrole-3-carbonylamino)methyl)phenyl)methylenecarbamate
(w) (Z)-propyl amino-(4-((1-(4-fluorophenyl)-2,5-dimethyl-pyrrole-3-carbonylamino)methyl)phenyl)methylenecarbamate
(x) (Z)-propyl amino-(4-((2,5-dimethyl-1-(4-pyridylmethyl)pyrrole-3-carbonylamino)methyl)phenyl)methylenecarbamate
(y) (Z)-propyl amino-(4-((1-benzylpyrazole-4-carbonylamino)methyl)phenyl)methylenecarbamate In another aspect, the present invention provides compounds having the formula:

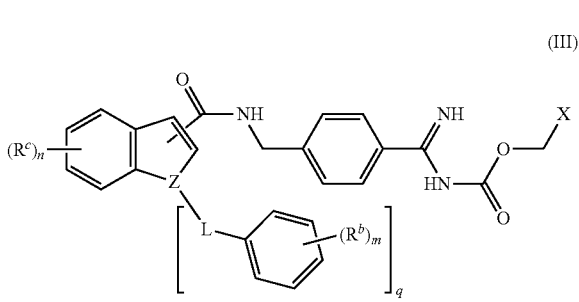

(III)

and pharmaceutically acceptable salts thereof, wherein the subscript m is an integer of from 0 to 5. The subscript n is an integer of from 0 to 4. The subscript q is an integer of from 0 to 1. In one embodiment, the subscript m is 0. In another embodiment, the subscript n is an integer from 0 to 2. In yet another embodiment, the subscript q is 0. In still another embodiment, the subscript q is 1.

L is a linking group selected from the group consisting of a bond, $CH_2$ and $SO_2$. In one embodiment, L is $CH_2$ or $SO_2$. X is a member selected from the group consisting of H, $C_{1-8}$ alkyl and phenyl.

Each of $R^b$ and $R^c$ is independently selected from the group consisting of cycloalkyl, haloalkyl, halogen, —OH, —$OR^2$, —$OSi(R^2)_3$, —$OC(O)O$—$R^2$, —$OC(O)R^2$, —$OC(O)NHR^2$, —$OC(O)N(R^2)_2$, —SH, —$SR^2$, —$S(O)R^2$, —$S(O)_2R^2$, —$SO_2NH_2$, —$S(O)_2NHR^2$, —$S(O)_2N(R^2)_2$, —$NHS(O)_2R^2$, —$NR^2S(O)_2R^2$, —$C(O)NH_2$, —$C(O)NHR^2$, —$C(O)N(R^2)_2$, —$C(O)R^2$, —$C(O)H$, —$C(=S)R^2$, —$NHC(O)R^2$, —$NR^2C(O)R^2$, —$NHC(O)NH_2$, —$NR^2C(O)NH_2$, —$NR^2C(O)NHR^2$, —$NHC(O)NHR^2$, —$NR^2C(O)N(R^2)_2$, —$NHC(O)N(R^2)_2$, —$CO_2H$, —$CO_2R^2$, —$NHCO_2R^2$, —$NR^2CO_2R^2$, —$R^2$, —CN, —$NO_2$, —$NH_2$, —$NHR^2$, —$N(R^2)_2$, —$NR^2S(O)NH_2$, —$NR^2S(O)_2NHR^2$, —$NH_2C(=NR^2)NH_2$, —$N=C(NH_2)NH_2$, —$C(=NR^2)NH_2$, —NH—OH, —$NR^2$—OH, —$NR^2$—$OR^2$, —N=C=O, —N=C=S, —$Si(R^2)_3$, —NH—$NHR^2$, —$NHC(O)NHNH_2$, NO, —N=C=$NR^2$ and —S—CN, wherein each $R^2$ is independently alkyl or aryl. In one embodiment, $R^2$ is $C_1$-$C_8$ alkyl. In another embodiment, $R^2$ is unsubstituted aryl, such as phenyl or pyridyl, or a substituted aryl, such as a substituted phenyl or a substituted pyridyl.

In one embodiment, each of $R^b$ and $R^c$ is independently selected from the group consisting of $C_1$-$C_8$ alkyl, $C_1$-$C_8$ alkoxy, aryl, aryl($C_1$-$C_8$ alkyl), halogen, —$NH_2$, —NH($C_1$-$C_8$ alkyl), —N($C_1$-$C_8$ alkyl)$_2$, —CN, —C(=O)($C_1$-$C_8$ alkyl), —C(=O)$NH_2$, —C(=O)NH($C_1$-$C_8$ alkyl), —C(=O)N($C_1$-$C_8$ alkyl)$_2$, —OH, —COOH, —COO($C_1$-$C_8$ alkyl), —OCO ($C_1$-$C_8$ alkyl), —O(C=O)O($C_1$-$C_8$alkyl)-$NO_2$, —SH, —S($C_1$-$C_8$ alkyl), —NH(C=O)($C_1$-$C_8$ alkyl), —NH(C=O)O($C_1$-$C_8$ alkyl), —O(C=O)NH($C_1$-$C_8$ alkyl), —$SO_2$($C_1$-$C_8$ alkyl), —$NHSO_2$($C_1$-$C_8$ alkyl) and —$SO_2NH$($C_1$-$C_8$ alkyl). In another embodiment, each of $R^b$ and $R^c$ is independently selected from the group consisting of $C_1$-$C_8$ alkyl, $C_1$-$C_8$ alkoxy, phenyl, phenyl($C_1$-$C_8$ alkyl), halogen, —CN, —$NH_2$, —NH($C_1$-$C_8$ alkyl), —N($C_1$-$C_8$ alkyl)$_2$, —C(=O)$CH_3$, —C(=O)$NH_2$, —OH, —COOH, —COO($C_1$-$C_8$ alkyl), —OCO($C_1$-$C_8$ alkyl), —O(C=O)O($C_1$-$C_8$alkyl), —$NO_2$, —SH, —S($C_1$-$C_8$ alkyl), and —NH(C=O)($C_1$-$C_8$alkyl). In yet another embodiment, each of $R^b$ and $R^c$ is independently selected from the group consisting of $C_1$-$C_8$ alkyl, $C_1$-$C_8$ alkoxy, phenyl, phenyl($C_1$-$C_8$ alkyl), phenoxy, aryloxy, halogen, —CN, —$NH_2$, —NH-aryl, —(C=O)$CH_3$, —(C=O)$NH_2$, —OH, —COOH, —COO($C_1$-$C_8$ alkyl), —OCO($C_1$-$C_8$ alkyl), —COO-aryl, —OC(O)-aryl, —O(C=O)O($C_1$-$C_8$alkyl)-$NO_2$, —SH, —S($C_1$-$C_8$ alkyl), —NH(C=O)($C_1$-$C_8$alkyl) and the like.

When q is 0, Z is a member selected from the group consisting of O, S and $NR^d$ wherein $R^d$ is H or $C_1$-$C_8$ alkyl. When q is 1, Z is N. In one embodiment, the subscript q is 0 and Z is selected from the group consisting of O, S and NH. In one instance, the subscript n is 0, 1 or 2. In one occurrence, Z is O or S. In another embodiment, the subscript q is 1. In one instance, L is $CH_2$ or $SO_2$.

In each instance or occurrence, X is a member selected from the group consisting of H, $C_{1-8}$ alkyl and phenyl.

In one embodiment, the compounds of formula III have a subformula IIIa:

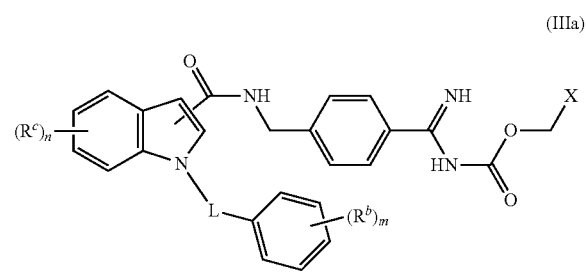

(IIIa)

Substituents $R^b$ and $R^c$ and subscripts m and n are as defined above. In one instance, L is $CH_2$. In another instance, L is $SO_2$. In yet another instance, m is 0. In still another instance, n is 0.

In another embodiment, compounds of formula III have a subformula IIIa-1:

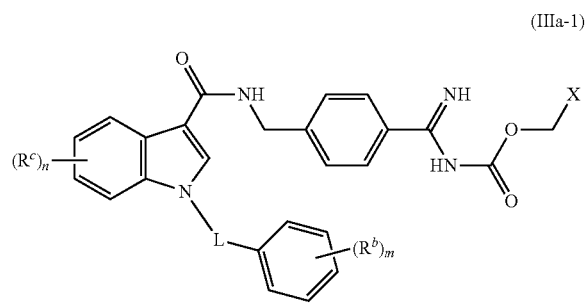

(IIIa-1)

The following are mentioned as examples of particularly preferred compounds of general formula III:

(a) (Z)-methyl amino-(4-((1-benzylindole-3-carbonylamino) methyl)phenyl)methylenecarbamate (b) (Z)-methyl amino-(4-(1-(benzenesulfonyl)indole-3-carbonylamino)methyl)phenyl)methylenecarbamate (c) (Z)-ethyl amino-(4-((1-benzylindole-3-carbonylamino) methyl)phenyl)methylenecarbamate (d) (Z)-ethyl amino-(4-(1-(benzenesulfonyl)indole-3-carbonylamino)methyl)phenyl)methylenecarbamate In another aspect, the present invention provides compounds of the general formula V:

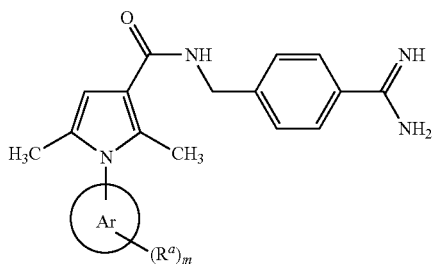
(V)

wherein Ar is a ring selected from benzene, pyridine, pyrimidine or a five-membered heteroaryl ring, $R^a$ has the same meaning as in general formula I, and m is an integer of 1-5 when Ar is benzene, 0-4 when Ar is pyridine, 0-3 when Ar is pyrimidine, and 0-2 when Ar is a five-membered heteroaryl ring.

The following are provided as examples of particularly preferred compounds of general formula V:
(a) N-[(4-carbamimidoylphenyl)methyl]-1-(4-fluorophenyl)-2,5-dimethyl-pyrrole-3-carboxamide
(b) N-[(4-carbamimidoylphenyl)methyl]-1-(2-fluorophenyl)-2,5-dimethyl-pyrrole-3-carboxamide
(c) N-[(4-carbamimidoylphenyl)methyl]-1-(4-methoxyphenyl)-2,5-dimethyl-pyrrole-3-carboxamide
(d) N-[(4-carbamimidoylphenyl)methyl]-1-(4-chlorophenyl)-2,5-dimethyl-pyrrole-3-carboxamide
(e) N-[(4-carbamimidoylphenyl)methyl]-1-(2,3-dihydro-1,4-benzodioxin-6-yl)-2,5-dimethyl-pyrrole-3-carboxamide
(f) N-[(4-carbamimidoylphenyl)methyl]-2,5-dimethyl-1-(3-pyridyl)pyrrole-3-carboxamide
(g) N-[(4-carbamimidoylphenyl)methyl]-2,5-dimethyl-1-(2-pyridyl)pyrrole-3-carboxamide
(h) N-[(4-carbamimidoylphenyl)methyl]-2,5-dimethyl-1-thiazol-2-yl-pyrrole-3-carboxamide.

Compounds of general formula V can be prepared using methods described herein and augmented by methods described in U.S. Pat. No. 7,625,944. Compounds (a)-(h) disclosed above possess exceptional and unanticipated properties as inhibitors of plasma kallikrein (PK), in that they exhibit inhibition constants ($K_i$) towards PK of less than $10^{-7}$ M ($K_i < 0.1$ μM), thus being especially potent inhibitors of this enzyme.

One of skill in the art will appreciate that compounds of formula I, Ia, Ib, III, IIIa and IIIa-1, can exist in tautomeric form as indicated below, and both forms are considered to be within the scope of the expressed generic formulae:

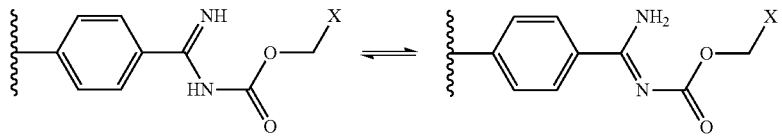

wherein the wavy line indicates that attachment to the remainder of the compound (in formulae I, Ia, Ib, III, IIIa or IIIa-1).

Preparation of Compounds

There are various synthetic routes by which a skilled artisan can prepare the compounds and intermediates of the present invention. The scheme shown below provides one such exemplary route. Other routes or modification of the routes would be readily apparent to a skilled artisan and within the scope of the present invention.

Scheme I. Preparation of Compounds of General Formula I:

1 mmol of a compound of general formula II and 6 mmol of potassium carbonate is dissolved in 6 ml of water and 30 ml of tetrahydrofuran (THF). The mixture is stirred vigorously, and 1 mmol of Cl—C(=O)—O—CH$_2$—X added (X=H, $C_{1-8}$ alkyl, or phenyl. The stirring is continued for 60 min, and then the organic layer removed and dried in vacuo to obtain the corresponding compound of general formula I.

Scheme 1

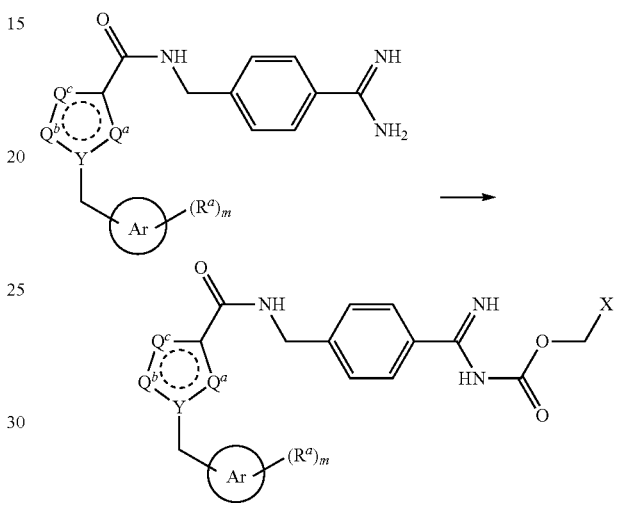

In the reaction described above, any reactive groups present on the compound of general formula I, such as hydroxyl, carboxy, amino, alkylamino or imino group may be protected during the reaction by conventional protecting groups well-known to skilled artisans, which can be subsequently removed by well-known chemical methods after the reaction is completed.

IV. Pharmaceutical Compositions

In addition to having compounds of formula I and III provided above, the compositions for prevention and treatment of plasma kallikrein-related diseases or conditions in humans and animals typically contain a pharmaceutical carrier, excipient and diluent.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier, which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation.

In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, oleagino-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles, as well as eye-drops for opthalmological use.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiments, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. patent application Ser. No. 08/746,404, filed Nov. 8, 1996 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, poly-phosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable copolymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1, the entire disclosure of which is incorporated in its entirety.

Moreover, as described for example in U.S. Pat. No. 6,770,729, which is incorporated herein in its entirety, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release an inhibitory agent in response to a decrease in the pH of the polymer composition. Alternatively, certain polymer compositions can be designed to release the inhibitory agent in response to the presence of hydrogen peroxide.

V. Plasma Kallikrein-dependent Diseases or Conditions

Plasma kallikrein (PK), a serine protease present in plasma as the inactive zymogen precursor plasma prekallikrein (prePK), is proteolytically activated by FXIIa. In a positive feedback loop, PK proteloytically activates the zymogen FXII, leading to additional FXIIa formation, further amplifying its own activation. FXIIa also activates the zymogen FXI to active FXIa, which results in the initiation of the intrinsic (contact) pathway of blood coagulation, resulting in generation of thrombin, and cleavage of fibrinogen. Importantly, PK cleaves high molecular weight kininogen (HMWK) to generate bradykinin. Bradykinin is able to open the tight junctions between endothelial cells lining blood vessels by activating its receptors, B1 and B2, present on the endothelial cells' surface, and thus allowing fluid and plasma protein to extravasate into tissue, a condition known as increased vascular permeability. Disruption of tight junctions of the blood-brain barrier, and consequent leakage of plasma and proteins into the brain (edema) have also been associated with neurodegenerative diseases, such as Alzheimer's Disease, Parkinson's Disease, and multiple sclerosis (MS), as well as with CNS infections and brain tumors. For example, peritumoral brain edema results in poorer prognosis in patients with glioblastoma multiforme (Schoenegger K, Oberndorfer S, *Eur J Neurol.* 2009 July; 16(7):874-8). The increased vascular permeability caused by bradykinin formation can result in the accumulation of excess fluid (edema) in many tissues and organs in various diseases, e.g., angioedema, cystoid macular edema, diabetic macular edema, macular edema after retinal vein occlusion, cerebrovascular edema following stroke or head trauma, and capillary leak syndrome. For example, the PK inhibitor ASP-440 (already known from WO 2008/016883, and U.S. Pat. No. 7,625,944) has been shown to reduce retinal vascular permeability in angiotensin-II-treated rodents, as did the BK receptor antagonist Hoe-140 (Phipps, J. A., et al. (2009) *Hypertension* 53: 175-181). Activation of prePK and the contact system has also been shown to cause anaphylaxis, e.g., in patients treated with contaminated heparin (Kishimoto, T. K., et al. (2008) *N. Engl. J. Med.* 358: 2457-2467).

For example, the importance of BK in vasogenic edema is further illustrated in hereditary angioedema, in which individuals have little or no functional C1-Inhibitor, the major endogenous inhibitor of PK. High levels of bradykinin are generated in these individuals resulting in extravasation of fluid and protein from the plasma into soft tissue, thus causing life-threatening edema.

For example, bradykinin and its receptors have been shown to be involved in tumor angiogenesis (Ikeda, Y., et al. (2004) *Cancer Research* 64: 5178-5185), pulmonary hypertension (Taraseviciene-Stewart, L., et al. (2005) *Peptides* 26: 1292-1300), and asthma (Barnes, P. J., (1992) *Recent Progress on Kinins*, AAS38/III, Birkhauser Verlag Basel).

For example, C1-Inhibitor is also known to be involved in the pathogenesis of age-related macular degeneration (Ennis, S., et al. (2008) *Lancet* 372: 1828-1834) and ischemia-reperfusion injury following organ transplant or mycocardial infarction (Inderbitzin, D., et al. (2004) *Eur. Surg. Res.* 36: 142-147; Horstick, G., et al. (2001) *Circulation* 104: 3125-3131).

For example, in patients with angioedema conditions, a small polypeptide PK inhibitor (DX-88, ecallantide) alleviates edema in patients with hereditary angioedema (Williams, A. et al. (2003) *Transfus. Apher. Sci.* 29: 255-258; Schneider, L. et al. (2007) *J Allergy Clin Immunol.* 120(2):416-22; Levy, J. H. et al. (2006) *Expert Opin. Invest. Drugs* 15: 1077-1090). A bradykinin B2 receptor antagonist, icatibant, is also effective in treating hereditary angioedema (Bork, K. et al. (2007) *J. Allergy Clin. Immunol.* 119: 1497-1503). PK generates bradykinin, therefore inhibition of PK would inhibit bradykinin production.

For example, in thrombogenesis resulting from fibrinolytic treatment (e.g. tissue plasminogen activator, streptokinase), higher levels of PK are found in patients undergoing fibrinolysis (Hoffmeister, H. M. et al. (1998) *J. Cardiovasc. Pharmacol.* 31: 764-72). Plasmin-mediated activation of the intrinsic pathway has been shown to occur in plasma and blood and was markedly attenuated in plasma from individuals deficient in any of the intrinsic pathway components (Ewald, G. A. et al. (1995) *Circulation* 91: 28-36).

For example, individuals who have had an acute MI were found to have elevated levels of activated PK and thrombin (Hoffmeister, H. M., et al. (1998) *Circulation* 98: 2527-33).

For example, DX-88 reduced brain edema, infarct volume and neurological deficits in an animal model of ischemic stroke (Storini, C., et al. (2006) *J. Pharm. Exp. Ther.* 318: 849-854). C1-INH reduced infarct size in a mouse model of middle cerebral artery occlusion (De Simoni, M. G., et al. (2004) *Am. J. Pathol.* 164: 1857-1863; Akita, N., et al. (2003) *Neurosurgery* 52: 395-400). For example, the PK inhibitor ASP-440 was shown to reduce infarction volume and cerebrovascular edema in a rat model of ischemic stroke, and expansion of intracerebral hemorrhage in a model of hemorrhagic stroke (Methods for Treatment of Kallikrein-Related Disorders, WIPO, PCT WO 2009/0971). B2 receptor antagonists were found to reduce the infarct volume, brain swelling and neutrophil accumulation and were neuroprotective in an animal model of ischemic stroke (Zausinger, S., et al., (2003) *Acta Neurochir. Suppl.* 86: 205-207; Lumenta, D. B., et al. (2006) *Brain Res.* 1069: 227-234; Ding-Zhou, L., et al. (2003) *Br. J. Pharmacol.* 139: 1539-1547).

Regarding complications associated with cardiopulmonary bypass (CPB) surgery, it has been found that the contact system is activated during CPB (Wachtfogel, Y. T. (1989) *Blood* 73: 468) consequently resulting in up to a 20-fold increase in plasma bradykinin (Cugno, M. et al. (2006) *Chest* 120: 1776-1782; and Campbell, D. J. et al. (2001) *Am. J.*

Physiol. Reg. Integr. Comp. Physiol. 281: 1059-1070). Capillary leak syndrome associated with CPB can be reduced using a PK inhibitor (Mojcik, C. F., Levy, J. H., *Ann Thorac Surg.* 2001 February; 71(2):745-54).

For example, PK inhibitors, P8720 and PKSI-527 have also been found to reduce joint swelling in rat models of arthritis (see, De La Cadena, R. A. et al. (1995) *FASEB J.* 9: 446-452; Fujimori, Y. (1993) *Agents Action* 39: 42-48). It has also been found that inflammation in animal models of arthritis was accompanied by activation of the contact system (Blais, C. Jr. et al. (1997) *Arthritis Rheum.* 40: 1327-1333).

For example, the PK inhibitor P8720 has been found to reduce inflammation in an acute and chronic rat model of inflammatory bowel disease, IBD (Stadnicki, A. et al. (1998) *FASEB J,* 12(3):325-33; Stadnicki, A. et al. (1996) *Dig. Dis. Sci.* 41: 912-920; De La Cadena, R. A., et al. (1995) *FASEB J.* 9: 446-452). The contact system is activated during acute and chronic intestinal inflammation (Sartor, R. B. et al. (1996) *Gastroenterology* 110: 1467-1481). It has been found that a B2 receptor antagonist, an antibody to high molecular weight kininogen or reduction in levels of kininogen reduced clinicopathology in animal models of IBD (Sartor, R. B. et al. (1996) *Gastroenterology* 110: 1467-1481; Arai, Y. et al. (1999) *Dig. Dis. Sci.* 44: 845-851; Keith, J. C. et al. (2005) *Arthritis Res. Therapy* 7: R769-R776).

For example, H-D-Pro-Phe-Arg-CMK, an inhibitor of PK and FXIIa, as well as C1-Inhibitor have been shown to reduce vascular permeability in multiple organs and reduce lesions in LPS or bacterial induced sepsis in animals (Liu, D. et al. (2005) *Blood* 105: 2350-2355; Persson, K. et al. (2000) *J. Exp. Med.* 192: 1415-1424). Clinical improvement was observed in sepsis patients treated with C1-Inhibitor (Zeerleder, S. et al. (2003) *Clin. Diagnost. Lab. Immunol.* 10: 529-535; Caliezi, C., et al. (2002) *Crit. Care Med.* 30: 1722-8; and Marx, G. et al. (1999) *Intensive Care Med.* 25: 1017-20). Fatal cases of septicemia are found to have a higher degree of contact activation (Martinez-Brotons, F. et al. (1987) *Thromb. Haemost.* 58: 709-713; Kalter, E. S. et al. (1985) *J. Infect. Dis.* 151: 1019-1027).

For example, it has been found that prePK levels are higher in diabetics, especially those with proliferative retinopathy, and correlate with fructosamine levels (Gao, B.-B., et al. (2007) *Nature Med.* 13: 181-188; Kedzierska, K. et al. (2005) *Archives Med. Res.* 36: 539-543). PrePK is also found to be elevated in diabetics and is highest in those with a sensomotor neuropathy (Christie, M. et al. (1984) *Thromb. Haemostas.* 52: 221-223). PrePK levels are elevated in diabetics and are associated with increased blood pressure, independently correlate with the albumin excretion rate, and are elevated in diabetics with macroalbuminuria suggesting prePK may be a marker for progressive nephropathy (Jaffa, A. A. et al. (2003) *Diabetes* 52: 1215-1221). B1 receptor antagonists have been found to decrease enhanced vascular permeability and plasma leakage into various organs, including the skin and retina, in rats with streptozotocin-induced diabetes (Lawson, S. R. et al. (2005) *Eur. J. Pharmacol.* 514: 69-78; Lawson S R, Gabra B H, et al (2005) *Regul Pept.* 124:221-4). B1 receptor antagonists can also prevent streptozotocin-treated mice from developing hyperglycemia and renal dysfunction (Zuccollo, A., et al. (1996) *Can. J. Physiol. Pharmacol.* 74: 586-589).

Therefore, diseases or conditions that can be treated using the compounds of the present invention include, but are not limited to, ischemic stroke, hemorrhagic stroke, hypertension and its vascular complications (especially retinopathy and nephropathy), cerebrovascular edema, pulmonary hypertension, inflammation, pain, acute myocardial infarction (MI), deep vein thrombosis (DVT), complications from fibrinolytic treatment (e.g., with tissue plasminogen activator, streptokinase) following stroke or MI, angina, angioedema, sepsis, arthritis, complications of cardiopulmonary bypass, capillary leak syndrome, inflammatory bowel disease, diabetes and its vascular complications (especially retinopathy, diabetic macular edema, nephropathy and neuropathy), age-related macular degeneration, retinal vein occlusions, brain edema, ischemia-reperfusion injury, angiogenesis (e.g., in cancer), asthma, anaphylaxis, and cerebrovascular complications of neurological conditions (e.g., Alzheimer's Disease, Parkinson's Disease, multiple sclerosis, CNS infections, and glioblastoma multiforme).

Upon administration to a subject in need thereof, the pro-drug compounds of general formulae I and III of the present invention will be converted in vivo into PK inhibitors, and therefore lead to inhibition of both the intrinsic pathway of blood coagulation, as well as the formation of bradykinin from high molecular weight kininogen. In this regard, the pro-drug compounds of the present invention have many pharmaceutical advantages. One advantage is in that their administration to a subject via most clinically useful routes, e.g., oral, subcutaneous, topical (including opthalmological eye-drops), intravitreal etc., will result in higher levels of PK inhibitor compound in plasma or the disease-affected organ (e.g., the eye) when compared to administration of the corresponding PK inhibitor compound (already known from WO 2008/016883, and U.S. Pat. No. 7,625,944) at a similar dose. This would result in a greater extent of inhibition of PK in vivo, and therefore a larger therapeutic effect. Another advantage is that their administration via routes such as subcutaneous, intramuscular or topical, will result in a slower appearance of the PK inhibitor compound in plasma or the disease-affected organ (e.g., the eye), thus effectively prolonging the time-period over which therapeutically useful levels of compound will be maintained in vivo. Thus, less frequent dosing would be required to maintain therapeutic levels in a subject in need of treatment with a PK inhibitor.

The compounds of general formula V provided in the current invention also possess many advantages and novel properties over compounds disclosed in WO 2008/016883, and U.S. Pat. No. 7,625,944. Especially, such compounds possess high inhibitory activity towards PK, and as such, may be used for treatment of PK-related disease conditions that require potent inhibition of PK activity, such as in stroke or retinal vein occlusions. They also exhibit longer half-lives of elimination in vivo from plasma when administered via a subcutaneous route, and thus may be useful for treating PK-related disease conditions that require sustained inhibition of PK activity, such as diabetic macular edema.

The following examples are provided to illustrate various aspects of the present invention.

EXAMPLE 1

Preparation of (Z)-hexyl amino-(4-((1-benzylpyrazole-4-carbonylamino)methyl)phenyl)methylenecarbamate 30 mg of 1-benzyl-N-[(4-carbamimidoylphenyl)methyl]pyrazole-4-carboxamide hydrochloride and 35 mg of potassium carbonate were dissolved in 0.4 ml of water and 2 ml of tetrahydrofuran. The mixture was stirred at room temperature, and 0.013 ml of n-hexyl chloroformate (Sigma-Aldrich) added. Stirring was continued for 1 h, following which the organic layer was removed, and dried in vacuo to obtain the synthetic target (>90% yield). The mass of the compound was verified using LC/MS/MS.

Calculated mass: 461.6; Experimental mass (m+1): 462.5

EXAMPLE 2

Preparation of (Z)-hexyl amino-(4-((1-(4-fluorophenyl)-2,5-dimethyl-pyrrole-3-carbonylamino)methyl)phenyl)methylenecarbamate 48 mg of N-[(4-carbamimidoylphenyl)methyl]-1-(4-fluorophenyl)-2,5-dimethyl-pyrrole-3-carboxamide hydrochloride and 50 mg of potassium carbonate were dissolved in 0.6 ml of water and 3 ml of tetrahydrofuran. The mixture was stirred at room temperature, and 0.019 ml of n-hexyl chloroformate (Sigma-Aldrich) added. Stirring was continued for 1 h, following which the organic layer is removed, and dried in vacuo to obtain the synthetic target (>90% yield). The mass of the compound was verified using LC/MS/MS.

Calculated mass: 492.6; Experimental mass (m+1): 493.3

EXAMPLE 3

Preparation of (Z)-methyl amino-(4-((1-benzylpyrazole-4-carbonylamino)methyl)phenyl)methylenecarbamate 57 mg of 1-benzyl-N-[(4-carbamimidoylphenyl)methyl]pyrazole-4-carboxamide hydrochloride and 59 mg of potassium carbonate were dissolved in 0.72 ml of water and 3.6 ml of tetrahydrofuran. The mixture was stirred at room temperature, and 0.012 ml of methyl chloroformate (Sigma-Aldrich) added. Stirring is continued for 1 h, following which the organic layer is removed, and dried in vacuo to obtain the synthetic target. The mass of the compound was verified using LC/MS/MS.

Calculated mass: 391.2; Experimental mass (m+1): 392.2

EXAMPLE 4

Preparation of (Z)-methyl amino-(4-((1-(4-fluorophenyl)-2,5-dimethyl-pyrrole-3-carbonylamino)methyl)phenyl)methylenecarbamate 75 mg of N-[(4-carbamimidoylphenyl)methyl]-1-(4-fluorophenyl)-2,5-dimethyl-pyrrole-3-carboxamide hydrochloride and 78 mg of potassium carbonate were dissolved in 0.95 ml of water and 4.75 ml of tetrahydrofuran. The mixture was stirred at room temperature, and 0.016 ml of methyl chloroformate (Sigma-Aldrich) added. Stirring was continued for 1 h, following which the organic layer is removed, and dried in vacuo to obtain the synthetic target. The mass of the compound was verified using LC/MS/MS.

Calculated mass: 422.2; Experimental mass (m+1): 423.2

EXAMPLE 5

Preparation of (Z)-ethyl amino-(4-((1-(4-fluorophenyl)-2,5-dimethyl-pyrrole-3-carbonylamino)methyl)phenyl)methylenecarbamate 130 mg of N-[(4-carbamimidoylphenyl)methyl]-1-(4-fluorophenyl)-2,5-dimethyl-pyrrole-3-carboxamide hydrochloride and 130 mg of potassium carbonate were dissolved in 1.6 ml of water and 8 ml of tetrahydrofuran. The mixture was stirred at room temperature, and 0.031 ml of ethyl chloroformate (Sigma-Aldrich) added. Stirring was continued for 1 h, following which the organic layer is removed, and dried in vacuo to obtain the synthetic target. The mass of the compound was verified using LC/MS/MS.

Calculated mass: 436.2; Experimental mass (m+1): 437.2

EXAMPLE 6

Preparation of (Z)-propyl amino-(4-((1-(4-fluorophenyl)-2,5-dimethyl-pyrrole-3-carbonylamino)methyl)phenyl)methylenecarbamate 120 mg of N-[(4-carbamimidoylphenyl)methyl]-1-(4-fluorophenyl)-2,5-dimethyl-pyrrole-3-carboxamide hydrochloride and 120 mg of potassium carbonate were dissolved in 1.5 ml of water and 7.5 ml of tetrahydrofuran. The mixture was stirred at room temperature, and 0.034 ml of propyl chloroformate (Sigma-Aldrich) added. Stirring was continued for 1 h, following which the organic layer is removed, and dried in vacuo to obtain the synthetic target. The mass of the compound was verified using LC/MS/MS.

Calculated mass: 450.2; Experimental mass (m+1): 451.2

EXAMPLE 7

Preparation of (Z)-benzyl amino-(4-((1-(4-fluorophenyl)-2,5-dimethyl-pyrrole-3-carbonylamino)methyl)phenyl)methylenecarbamate 115 mg of N-[(4-carbamimidoylphenyl)methyl]-1-(4-fluorophenyl)-2,5-dimethyl-pyrrole-3-carboxamide hydrochloride and 115 mg of potassium carbonate were dissolved in 1.4 ml of water and 7 ml of tetrahydrofuran. The mixture was stirred at room temperature, and 0.04 ml of benzyl chloroformate (Sigma-Aldrich) added. Stirring was continued for 1 h, following which the organic layer is removed, and dried in vacuo to obtain the synthetic target. The mass of the compound was verified using LC/MS/MS.

Calculated mass: 498.2; Experimental mass (m+1): 499.2

EXAMPLE 8

Preparation of (Z)-ethyl amino-(4-((1-benzylpyrazole-4-carbonylamino)methyl)phenyl)methylenecarbamate 65 mg of 1-benzyl-N-[(4-carbamimidoylphenyl)methyl]pyrazole-4-carboxamide diacetate and 65 mg of potassium carbonate were dissolved in 0.75 ml of water and 3.75 ml of tetrahydrofuran. The mixture was stirred at room temperature, and 0.015 ml of ethyl chloroformate (Sigma-Aldrich) added. Stirring was continued for 1 h, following which the organic layer was removed, and dried in vacuo to obtain the synthetic target. The mass of the compound was verified using LC/MS/MS.

Calculated mass: 405.2; Experimental mass (m+1): 406.2

EXAMPLE 9

Conversion of (Z)-hexyl amino-(4-((1-benzylpyrazole-4-carbonylamino)methyl)phenyl)methylenecarbamate in vivo into 1-benzyl-N-[(4-carbamimidoylphenyl)methyl]pyrazole-4-carboxamide In order to demonstrate that the prodrugs of the present invention are converted in vivo into a known PK inhibitor, young male Sprague-Dawley rats were orally dosed with the prodrug compound (Z)-hexyl amino-(4-((1-benzylpyrazole-4-carbonylamino)methyl)phenyl)methylenecarbamate at 5 mg/kg in an aqueous solvent. Blood was removed at various time intervals via an arterial catheter into a citrated collection tube, and plasma generated by centrifugation. The concentration of the active compound I-benzyl-N-[(4-carbamimidoylphenyl)methyl]pyrazole-4-carboxamide in the plasma samples were determined using LC/MS/MS, and peak levels were found to be approximately 60 nM on average. The appearance of the active compound in plasma demonstrates that the prodrug compound was converted in vivo into the active compound.

EXAMPLE 10

Conversion of (Z)-ethyl amino-(4-((1-(4-fluorophenyl)-2,5-dimethyl-pyrrole-3-carbonylamino)methyl)phenyl)methylenecarbamate in vivo into N-[(4-carbamimidoylphenyl)methyl]-1-(4-fluorophenyl)-2,5-dimethyl-pyrrole-3-carboxamide Young male Sprague-Dawley rats were orally dosed with the pro-drug compound (Z)-ethyl amino-(4-((1-(4-fluorophenyl)-2,5-dimethyl-pyrrole-3-carbonyl amino)methyl)phenyl)methylenecarbamate at 5 mg/kg in an aqueous solvent. Blood was removed at various time intervals via an arterial catheter into a citrated collection tube, and plasma generated by centrifugation. The concentration of the active compound N-[(4-carbamimidoylphenyl)methyl]-1-(4-fluorophenyl)-2,5-dimethyl-pyrrole-3-carboxamide in the plasma samples were determined using LC/MS/MS, and peak levels were found to be approximately 120 nM on average. The appearance of the active compound in plasma demonstrates that the pro-drug compound was converted in vivo into the active compound.

EXAMPLE 11

Synthesis of N4-[(4-carbamimidoylphenyl)methyl]-1-(4-fluorophenyl)-2,5-dimethyl-pyrrole-3-carboxamide 808 mg (4 mmol) of 1-(4-fluorophenyl)-2,5-dimethyl-pyrrole-3-carboxylic acid (Enamine, Kiev, Ukraine) was dissolved in 100 ml methylene chloride and 30 ml dimethyl sulfoxide, and added with stirring to 4 g of PS-carbodiimide (Biotage, Charlotte, N.C., USA), substituted at 1.33 mmol/g, wetted with 40 ml methylene chloride. 892 mg (4 mmol) of 4-(aminomethyl)benzamidine hydrochloride (Astatech, Bristol, Pa., USA), and 540 mg of HOBt were dissolved in 50 ml dimethyl sulfoxide, added to the stirred mixture, followed by 1.4 ml of diisopropylethylamine (Sigma-Aldrich). The mixture was stirred for seven days at room temperature, followed by filtration to remove the consumed resin. 50 ml of water was added to 150 ml of the filtrate, stirred vigorously for 10 minutes, then allowed to settle for 20 minutes to separate aqueous phase from the methylene chloride. The aqueous phase was carefully removed, neutralized by adding Tris base to 20 mM final concentration, then applied to a 20 ml bed volume CM-Sepharose (Sigma-Aldrich) cation-exchange column equilibriated with 20 mM Tris-HCl, pH 8. The column was washed with 40 ml of methanol and then eluted with 40 ml of 5% formic acid in methanol. The target compound was recovered as a yellowish oily solid following removal of the solvent by evaporation. The mass of the compound was verified by LC-MS/MS.

Calculated mass: 364.2; Experimental mass (m+1): 365.2.

EXAMPLE 12

Synthesis of N-[(4-carbamimidoylphenyl)methyl]-1-(4-chlorophenyl)-2,5-dimethyl-pyrrole-3-carboxamide This was synthesized as described in Example 7, however using 1-(4-chlorophenyl)-2,5-dimethyl-pyrrole-3-carboxylic acid (Enamine, Kiev, Ukraine) as the starting carboxylic acid.

Calculated mass: 380.1; Experimental mass (m+1): 381.1.

EXAMPLE 13

Synthesis of N-[(4-carbamimidoylphenyl)methyl]-1-(4-methoxyphenyl)-2,5-dimethyl-pyrrole-3-carboxamide This was synthesized as described in Example 8, however using 1-(4-methoxyphenyl)-2,5-dimethyl-pyrrole-3-carboxylic acid (Enamine, Kiev, Ukraine) as the starting carboxylic acid.

Calculated mass: 376.2; Experimental mass (m+1): 377.1.

EXAMPLE 14

Human plasma kallikrein (PK) was obtained from Enzyme Research Laboratories (Gary, Ind.). The enzymatic activity of PK was assayed using the synthetic peptide substrate H-D-Pro-Phe-Arg-pNA (Bachem, Peninsula City, Calif.) with the cleavage of the substrate by the enzyme resulting in an increase in $A_{405}$, measured using a Molecular Devices $V_{max}$ Kinetic Microplate Reader. The uninhibited (control) activity of PK was determined by adding 190 µl of PK solution (2 nM in 0.05 M HEPES, pH 7.5, 0.01% Triton X-100) to 10 µl of H-D-Pro-Phe-Arg-pNA (2 mM in DMSO) in individual microtiter plate wells, mixed immediately by shaking, and the rate of increase in absorbance at 405 nm ($A_{405}$) determined over 120-180 sec. In parallel, compounds of general formula V were mixed in separate wells with the synthetic substrate to attain final concentrations of between 0.01-10 µM in the final 200 µl reaction mixture, and the reaction initiated by the addition of 190 µl of the PK solution. A diminished rate of cleavage in the presence of a compound of general formula V denotes inhibition of PK activity, and the apparent inhibition constant ($K_{i,app}$) of the interaction can be determined by using the following equation—

$$K_{i,app}=[I]/(PK_{Control}/PK_I-1)$$

where [I]=concentration of inhibitory compound, $PK_{Control}$=rate of substrate cleavage by uninhibited PK, $PK_I$=rate of substrate cleavage by PK in the presence of inhibitory compound.

The corrected $K_i$ of the interaction can be obtained as follows from the calculated $K_{i,app}$—

$$K_i=K_{i,app}/([S]/K_m+1)$$

Where [S]=concentration of synthetic substrate, and $K_m$=Michaelis constant of synthetic substrate for PK, in this case determined experimentally to be 0.33 mM under these conditions.

The table below shows the $K_i$ values of selected compounds of general formula V, determined using this method.

| Compound (General Formula V) | $K_i$, µM |
|---|---|
| N-[(4-carbamimidoylphenyl)methyl]-1-(4-fluorophenyl)-2,5-dimethyl-pyrrole-3-carboxamide | 0.013 |
| N-[(4-carbamimidoylphenyl)methyl]-1-(4-methoxyphenyl)-2,5-dimethyl-pyrrole-3-carboxamide | 0.017 |
| N-[(4-carbamimidoylphenyl)methyl]-1-(4-chlorophenyl)-2,5-dimethyl-pyrrole-3-carboxamide | 0.007 |
| N-[(4-carbamimidoylphenyl)methyl]-1-(2,3-dihydro-1,4-benzodioxin-6-yl)-2,5-dimethyl-pyrrole-3-carboxamide | 0.014 |

| Compound (General Formula V) | $K_i$, μM |
| --- | --- |
| N-[(4-carbamimidoylphenyl)methyl]-2,5-dimethyl-1-(3-pyridyl)pyrrole-3-carboxamide | 0.046 |
| N-[(4-carbamimidoylphenyl)methyl]-2,5-dimethyl-1-(2-pyridyl)pyrrole-3-carboxamide | 0.035 |
| N-[(4-carbamimidoylphenyl)methyl]-2,5-dimethyl-1-thiazol-2-yl-pyrrole-3-carboxamide | 0.068 |

EXAMPLE 15

Continuous infusion of the vasoconstrictor peptide angiotensin-II in Sprague-Dawley rats over 3-7 days using subcutaneously implanted Alzet minipumps results in elevated blood pressure, and is accompanied by increased retinal vascular permeability, which can be measured using the technique of vitreous fluorescein fluorophotometry, as described in the prior art (Clermont, A. C., et al (2006) *Invest Ophthalmol Vis Sci.;* 47: 2701-8). The plasma kallikrein inhibitor ASP-440 (U.S. Pat. No. 7,625,944) has been shown to be effective in reducing retinal vascular permeability in this animal model (Phipps, J. A., et al. (2009) *Hypertension* 53: 175-181). Inhibition of the excess retinal vascular permeability in this animal model following administration of compounds of the present invention via oral, subcutaneous, topical or intravitreal routes thus provides evidence of inhibition of plasma kallikrein in vivo. For example, administration of (Z)-methyl amino-(4-((1-(4-fluorophenyl)-2,5-dimethyl-pyrrole-3-carbonylamino)methyl)phenyl)methylenecarbamate by twice-daily oral gavage in this animal model for five days resulted in reduction of retinal vascular permeability by 55%. The ethyl prodrug, (Z)-ethyl amino-(4-((1-(4-fluorophenyl)-2,5-dimethyl-pyrrole-3-carbonylamino)methyl)phenyl)methylenecarbamate exhibited a similar level of activity.

What is claimed is:

1. A compound having the formula:

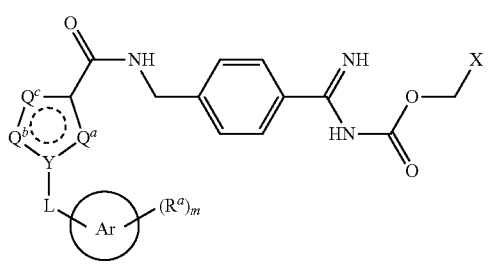

(I)

wherein
Ar is benzene, m is an integer from 0-5;
X is selected from the group consisting of H, $C_{1-8}$ alkyl and phenyl;

each $R^a$ is independently selected from the group consisting of halogen, —$OR^1$ and —$R^1$,
wherein each $R^1$ is independently alkyl;
L is a linking group selected from the group consisting of a bond and $CH_2$;
$Q^a$ and $Q^C$ are each $C(R^q)$ wherein each $R^q$ is independently selected from the group consisting of H, $C_{1-8}$ alkyl, and halogen;
$Q^b$ is N;
Y is N; and the ring having $Q^a$, $Q^b$, $Q^c$, and Y as ring vertices is a five-membered ring having two double bonds;
or a pharmaceutically acceptable salt thereof.

2. The compound of claim 1, wherein X is selected from the group consisting of H, methyl, ethyl and pentyl.

3. The compound of claim 1 wherein L is a bond.

4. The compound of 1 having the formula:

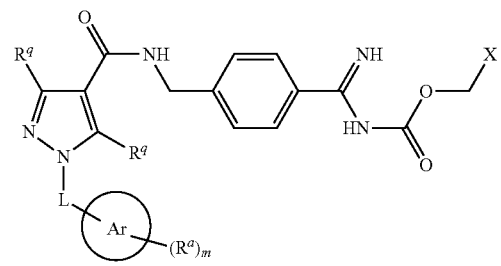

(Ib)

wherein Ar is a benzene ring and X is selected from the group consisting of H and $C_1$-$C_5$ alkyl.

5. The compound of claim 4, wherein each $R^q$ is independently selected from the group consisting of H, halogen and methyl.

6. The compound of claim 4, wherein L is —$CH_2$—.

7. The compound of claim 4, wherein Ar is a benzene ring, m is 0, each $R^q$ is H, and L is a bond.

8. The compound of claim 4, wherein Ar is a benzene ring, m is 0, each $R^q$ is H, and L is —$CH_2$—.

9. The compound of claim 1, selected from the group consisting of:
(a) (Z)-hexyl amino-(4-((1-benzylpyrazole-4-carbonylamino)methyl)phenyl)methylenecarbamate
(b) (Z)-methyl amino-(4-((1-benzylpyrazole-4-carbonylamino)methyl) phenyl)methylenecarbamate
(c)(Z)-benzyl amino-(4-((1-benzylpyrazole-4-carbonylamino)methyl) phenyl)methylenecarbamate
(d)(Z)-ethyl amino-(4-((1-benzylpyrazole-4-carbonylamino)methyl) phenyl)methylenecarbamate, and
(e)(Z)-propyl amino-(4-((1-benzylpyrazole-4-carbonylamino)methyl)phenyl)methylenecarbamate.

* * * * *